United States Patent
Gingrich et al.

(10) Patent No.: US 7,115,613 B2
(45) Date of Patent: *Oct. 3, 2006

(54) SELECTED FUSED PYRROLOCARBAZOLES

(75) Inventors: Diane E. Gingrich, Downingtown, PA (US); Robert L. Hudkins, Chester Springs, PA (US)

(73) Assignee: Cephalon, Inc., West Chester, PA (US)

( * ) Notice: Subject to any disclaimer, the term of this patent is extended or adjusted under 35 U.S.C. 154(b) by 86 days.

This patent is subject to a terminal disclaimer.

(21) Appl. No.: 10/400,136

(22) Filed: Mar. 26, 2003

(65) Prior Publication Data

US 2003/0203957 A1    Oct. 30, 2003

Related U.S. Application Data

(63) Continuation of application No. 09/935,285, filed on Aug. 22, 2001, now Pat. No. 6,630,500.

(60) Provisional application No. 60/278,455, filed on Mar. 23, 2001, provisional application No. 60/227,803, filed on Aug. 25, 2000.

(51) Int. Cl.
*A61K 31/505*    (2006.01)
*C07D 239/02*    (2006.01)

(52) U.S. Cl. .................. 514/256; 514/410; 544/298; 548/417

(58) Field of Classification Search ................ 514/410; 548/417

See application file for complete search history.

(56) References Cited

U.S. PATENT DOCUMENTS

| | | |
|---|---|---|
| 4,552,842 A | 11/1985 | Nettleton, Jr. et al. |
| 5,185,260 A | 2/1993 | Crissman et al. |
| 5,438,050 A | 8/1995 | Kleinschroth et al. |
| 5,475,110 A | 12/1995 | Hudkins et al. |
| 5,591,855 A | 1/1997 | Hudkins et al. |
| 5,594,009 A | 1/1997 | Hudkins et al. |
| 5,616,724 A | 4/1997 | Hudkins et al. |
| 5,705,511 A | 1/1998 | Hudkins et al. |
| 5,801,190 A | 9/1998 | Hudkins et al. |
| 5,808,060 A | 9/1998 | Hudkins et al. |

FOREIGN PATENT DOCUMENTS

| | | |
|---|---|---|
| WO | WO 98/07433 | 2/1998 |
| WO | WO 99/62523 | 12/1999 |
| WO | WO 00/18407 | 4/2000 |
| WO | WO 00/47583 | 8/2000 |

*Primary Examiner*—Kamal A. Saeed
(74) *Attorney, Agent, or Firm*—Christy Cheever

(57) ABSTRACT

The present invention relates generally to selected fused pyrrolocarbazoles, including pharmaceutical compositions thereof and methods of treating diseases therewith. The present invention is also directed to intermediates and processes for making these fused pyrrolocarbazoles.

8 Claims, No Drawings

SELECTED FUSED PYRROLOCARBAZOLES

This Application: is a continuation of U.S. Application Ser. No. 09/935,285 filed Aug. 22, 2001, now U.S. Pat. No. 6,630,500 which claims benefit of U.S. Provisional Application Ser. No. 60/227,803 filed Aug. 25, 2000 and U.S. Provisional Application Ser. No. 60/278,455 filed March 23, 2001.

FIELD OF THE INVENTION

The present invention relates generally to selected fused pyrrolocarbazoles, including pharmaceutical compositions thereof and methods of treating diseases therewith. The present invention is also directed to intermediates and processes for making these fused pyrrolocarbazoles.

BACKGROUND OF THE INVENTION

Publications cited throughout this disclosure are incorporated in their entirety herein by reference.

Various synthetic small organic molecules that are biologically active and generally known in the art as "fused pyrrolocarbazoles" have been prepared (See U.S. Pat. Nos. 5,475,110; 5,591,855; 5,594,009; and 5,616,724). In addition, U.S. Pat. No. 5,705,511 discloses fused pyrrolocarbazole compounds which possess a variety of functional pharmacological activities. The fused pyrrolocarbazoles were disclosed to be used in a variety of ways, including: enhancing the function and/or survival of cells of neuronal lineage, either singularly or in combination with neurotrophic factor(s) and/or indolocarbozoles; enhancing trophic factor-induced activity; inhibition of protein kinase C ("PKC") activity; inhibition of trk tyrosine kinase activity; inhibition of proliferation of a prostate cancer cell-line; inhibition of the cellular pathways involved in the inflammation process; and enhancement of the survival of neuronal cells at risk of dying.

The present inventors have found that certain selected fused pyrrolocarbazoles selected from the generic formulas of U.S. Pat. No. 5,705,511 but not specifically disclosed therein possess surprising and unexpected biological activities compared to the compounds described in U.S. Pat. No. 5,705,511.

SUMMARY OF THE INVENTION

Accordingly, one object of the invention is to provide novel fused pyrrolocarbazole compounds represented by the general Formula I:

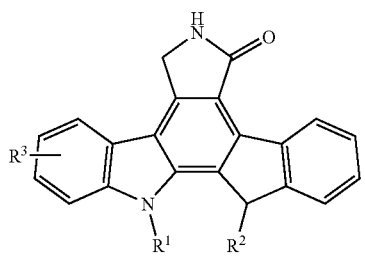

Formula I

Constituent members of Formula I are disclosed in detail, infra.

Preferred fused pyrrolocarbazoles are represented by the following Formula II:

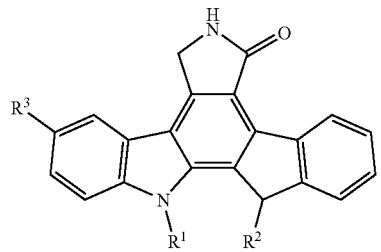

Formula II

Constituent members of Formula II are disclosed in detail, infra.

The fused pyrrolocarbazoles of the present invention may be used in a variety of ways, including: inhibition of angiogenesis; antitumor agents; enhancing the function and/or survival of cells of neuronal lineage, either singularly or in combination with neurotrophic factor(s) and/or indolocarbozoles; enhancing trophic factor-induced activity; inhibition of kinases; inhibition of vascular endothelial growth factor receptor (VEGFR) kinase, preferably VEGFR2; inhibition of mixed lineage kinase (MLK); trk kinase; inhibition of platelet derived growth factor receptor (PDGFR) kinase; inhibition of NGF-stimulated trk phosphorylation; inhibition of protein kinase C ("PKC") activity; inhibition of trk tyrosine kinase activity; inhibition of proliferation of a prostate cancer cell-line; inhibition of the cellular pathways involved in the inflammation process; and enhancement of the survival of neuronal cells at risk of dying. In addition, the fused pyrrolocarbazoles may useful for inhibition of c-met, c-kit, and mutated Flt-3 containing internal tandem duplications in the juxtamembrane domain. Because of these varied activities, the disclosed compounds find utility in a variety of settings, including research and therapeutic environments.

Another object of the present invention is to provide pharmaceutical compositions comprising a fused pyrrolocarbazole of the present invention wherein the compositions comprise a pharmaceutically acceptable excipient or carrier and a therapeutically effective amount of at least one of the compounds of the present invention, or a pharmaceutically acceptable salt or ester form thereof.

It is another object of the present invention to provide methods of treating or preventing diseases or disorders comprising administering a therapeutic or preventative effective amount of at least one of the compounds of the present invention to a subject in need thereof.

These and other objects, features and advantages of the fused pyrrolocarbazoles will be disclosed in the following detailed description of the patent disclosure.

DETAILED DESCRIPTION OF PREFERRED EMBODIMENTS

One embodiment of the present invention are the fused pyrrolocarbazoles represented by Formula I:

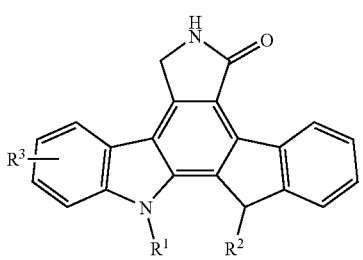

Formula I

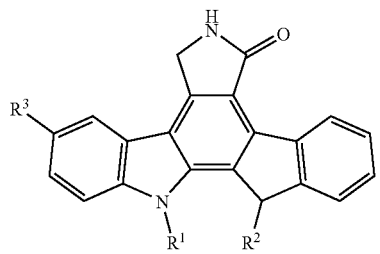

Formula II wherein:

R$^1$ and R$^2$ are the same or different and are independently selected from H, or alkyl of 1–8 carbons (inclusive), preferably an alkyl of 1–4 carbons (inclusive), substituted with OH, or —OR$^4$ where R$^4$ is an alkyl of 1–4 carbons (inclusive), aryl, preferably phenyl or naphthyl, or the residue of an amino acid after the hydroxyl group of the carboxyl group is removed; and R$^3$ is —CH$_2$OH; —CH$_2$OR$^7$; —(CH$_2$)$_n$SR$^5$; —(CH$_2$)$_n$S(O)$_y$R$^5$; —CH$_2$SR$^5$; or alkyl of 1–8 carbons (inclusive), preferably an alkyl of 1–4 carbons (inclusive), substituted with —OH, —OR$^5$, —OR$^8$, —CH$_2$OR$^7$, —S(O)$_y$R$^6$ or SR$^6$; and wherein R$^5$ is alkyl of 1–4 carbons (inclusive), or aryl, preferably phenyl or naphthyl;

R$^6$ is H, alkyl of 1–4 carbons (inclusive), aryl of 6–10 carbons, preferably phenyl or naphthyl, or heteroaryl;

R$^7$ is H or alkyl of 1–4 carbons (inclusive);

R$^8$ is the residue of an amino acid after the hydroxyl group of the carboxyl group is removed;

n is an integer of 1–4 (inclusive); and y is 1 or 2.

In certain preferred embodiments, the compounds of Formula I are those of Formula II:

wherein R$^1$, R$^2$, and R$^3$ are as defined for Formula I above.

In certain referred embodiments, R$^1$ is an alkyl of 1–4 carbons (inclusive), substituted with —OH or —OR$^4$ where R$^4$ is an alkyl of 1–4 carbons (inclusive), aryl, preferably phenyl or naphthyl, or the residue of an amino acid after the hydroxyl group of the carboxyl group is removed;

R$^2$ is H; and R$^3$ is —CH$_2$OH; —CH$_2$OR$^7$; —(CH$_2$)$_n$SR$^5$; —(CH$_2$)$_n$S(O)$_y$R$^5$; —CH$_2$SR$^5$; or alkyl of 1–8 carbons (inclusive), preferably an alkyl of 1–4 carbons (inclusive), substituted with —OH, —OR$^5$, —OR$^8$, —CH$_2$OR$^7$, —S(O)$_y$R$^6$ or SR$^6$;

wherein R$^5$, R$^6$, R$^7$ and R$^8$ are as defined for Formula I above.

In certain other preferred embodiments, R$^1$ is —CH$_2$CH$_2$CH$_2$OH or —CH$_2$CH$_2$CH$_2$OCOCH$_2$N(CH$_3$)$_2$, R$^2$ is H and R$^3$ is —CH$_2$OR$^7$; wherein R$^7$ is alkyl of 1–4 carbons (inclusive).

In certain even further preferred embodiments the fused pyrrolocarbazoles of Formula I and Formula II are those represented in Table I:

TABLE I

| Cmpd | R$^1$ | R$^2$ | R$^3$ |
|---|---|---|---|
| 1 | CH$_2$CH$_2$CH$_2$OH | H | CH$_2$OCH$_2$CH$_3$ |
| 2 | CH$_2$CH$_2$CH$_2$OH | H | CH$_2$OCH$_3$ |
| 3 | CH$_2$CH$_2$CH$_2$OH | H | CH$_2$OCH(CH$_3$)$_2$ |
| 4 | CH$_2$CH$_2$CH$_2$OH | H | CH$_2$OCH(CH$_3$)CH$_2$CH$_3$ |
| 5 | CH$_2$CH$_2$CH$_2$OH | H | (S)-CH$_2$OCH(CH$_3$)CH$_2$CH$_3$ |
| 6 | CH$_2$CH$_2$CH$_2$OH | H | (R)-CH$_2$OCH(CH$_3$)CH$_2$CH$_3$ |
| 7 | CH$_2$CHOHCH$_3$ | H | CH$_2$OCH$_2$CH$_3$ |
| 8 | CH$_2$CH$_2$CH$_2$OH | H | CH$_2$OCH$_2$CH$_2$CH$_3$ |
| 9 | CH$_2$CH$_2$CH$_2$OH | H | CH$_2$OCH$_2$CH$_2$CH$_2$CH$_3$ |
| 10 | CH$_2$CH$_2$CH$_2$OH | H | CH(CH$_3$)OCH$_2$CH$_3$ |
| 11 | CH$_2$CH$_2$CH$_2$OH | H | (chiral) CH(CH$_3$)OCH$_2$CH$_3$ |
| 12 | CH$_2$CH$_2$CH$_2$OH | H | (chiral) CH(CH$_3$)OCH$_2$CH$_3$ |
| 13 | CH$_2$CH$_2$CH$_2$OH | H | CH(CH$_3$)OCH$_3$ |
| 14 | H | CH$_2$CHOHCH$_3$ | CH$_2$OCH$_2$CH$_3$ |
| 15 | CH$_2$CH$_2$CH$_2$OH | H | CH(CH$_3$)OCH$_2$CH$_2$CH$_3$ |
| 16 | CH$_2$CH$_2$CH$_2$OH | H | CH(CH$_3$)OCH(CH$_3$)$_2$ |
| 17 | CH$_2$CH$_2$CH$_2$OH | H | CH$_2$OC(CH$_3$)$_3$ |
| 18 | CH$_2$CH$_2$CH$_2$OCOCH$_2$NH$_2$ | H | CH$_2$OCH(CH$_3$)$_2$ |
| 19 | CH$_2$CH$_2$CH$_2$OCOCH(NH$_2$)CH$_2$—CH$_2$CH$_2$NH$_2$ | H | CH$_2$OCH(CH$_3$)$_2$ |
| 20 | CH$_2$CH$_2$CH$_2$OCOCH$_2$CH$_2$NH$_2$ | H | CH$_2$OCH(CH$_3$)$_2$ |
| 21 | CH$_2$CH$_2$CH$_2$OCOCH$_2$CH$_2$—CH$_2$N(CH$_3$)$_2$ | H | CH$_2$OCH(CH$_3$)$_2$ |
| 22 | CH$_2$CH$_2$CH$_2$OCOCH$_2$N(CH$_3$)$_2$ | H | CH$_2$OCH(CH$_3$)$_2$ |
| 23 | CH$_2$CH$_2$CH$_2$OCOCH$_2$CH$_2$CH$_2$—CH$_2$CH$_2$NH$_2$ | H | CH$_2$OCH(CH$_3$)$_2$ |
| 24 | CH$_2$CH$_2$OH | H | CH$_2$SCH$_2$CH$_3$ |
| 25 | CH$_2$CH$_2$CH$_2$OH | H | CH$_2$SCH$_2$CH$_3$ |

TABLE I-continued

| Cmpd | R¹ | R² | R³ |
|---|---|---|---|
| 26 | CH₂CH₂CH₂OH | H | CH₂S(O)CH(CH₃)₂ |
| 27 | CH₂CH₂CH₂OH | H | CH₂SCH(CH₃)₂ |
| 28 | CH₂CH₂OH | H | CH₂OH |
| 29 | CH₂CH₂CH₂OH | H | CH₂OH |
| 30 | H | H | CH₂OH |
| 31 | H | H | CH₂OCH₂CH₃ |
| 32 | H | H | CH₂OCH(CH₃)₂ |
| 33 | CH₂CH₂CH₂OH | H | CH(OH)CH₃ |
| 34 | CH₂CH₂CH₂OH | H | CH(OH)CH₂CH₃ |
| 35 | H | H | CH(OH)CH₃ |
| 36 | H | H | (+/−) CH(OCH₃)CH₃ |
| 37 | CH₂CH₂CH₂OCOCF₃ | H | CH₂SCH₂CH₂CH₃ |
| 38 | CH₂CH₂CH₂OH | H | CH₂S(2-pyridyl) |
| 39 | CH₂CH₂CH₂OH | H | CH₂S(2-pyrimidyl) |
| 40 | CH₂CH₂CH₂OH | CH₂OH | CH₂OCH(CH₃)₂ |

Preferred fused pyrrolocarbazoles of Formula II are represented structurally in Table II:

TABLE II

| Compound | Structure |
|---|---|
| 1 | (structure) |
| 2 | (structure) |
| 3 | (structure) |
| 4 | +/− (structure) |
| 5 | (S) (structure) |
| 6 | (R) (structure) |

TABLE II-continued

| Compound | Structure |
|---|---|
| 7 | 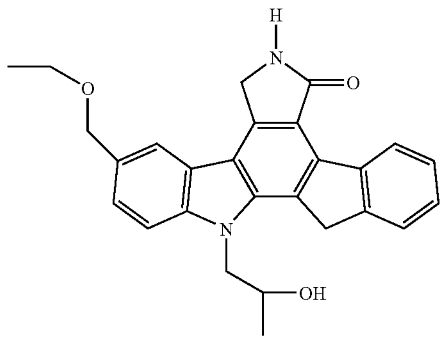 |
| 8 | 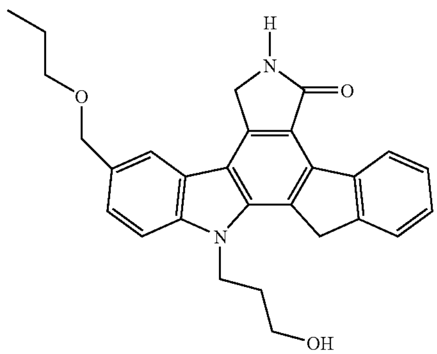 |
| 9 | 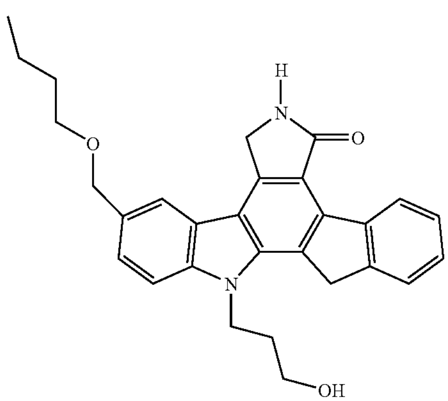 |
| 10 (+/−) | |
| 11 chiral | |
| 12 chiral | |
| 13 (+/−) | |
| 14 | 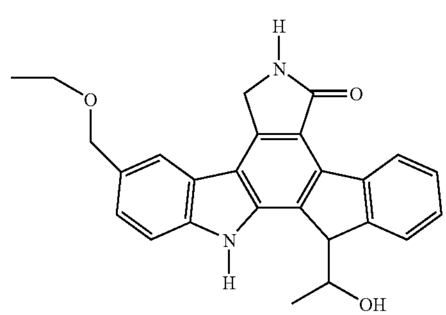 |

TABLE II-continued
| Compound | Structure |
|---|---|
| 15 | 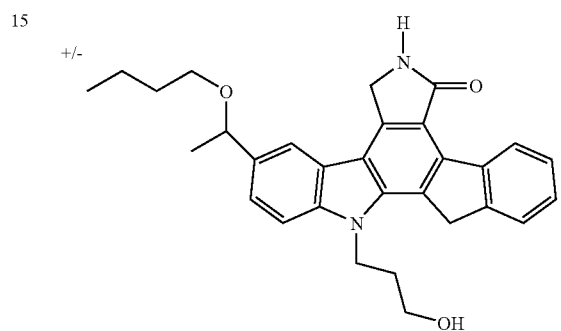 |
| 16 | 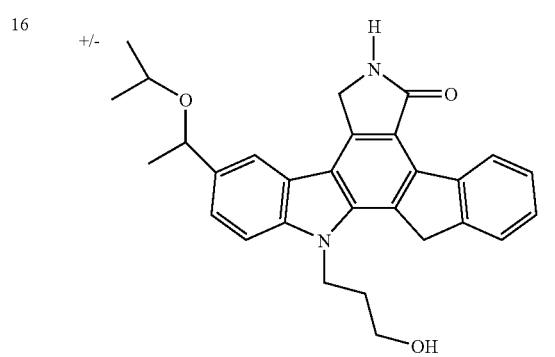 |
| 17 | 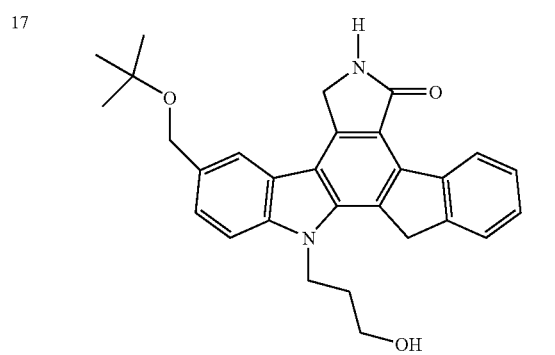 |
| 18 | 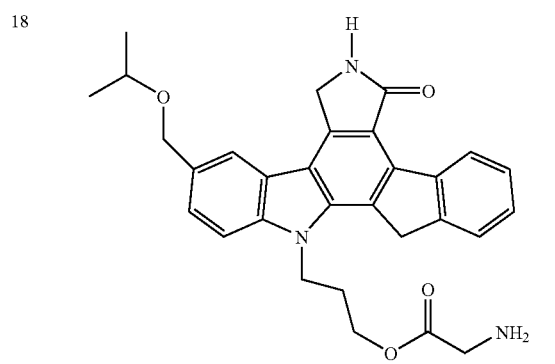 |
| 19 | 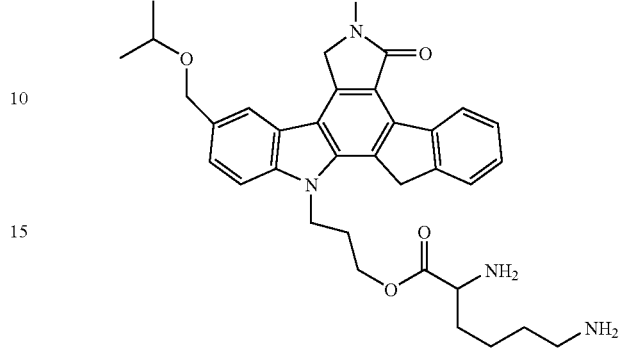 |
| 20 | 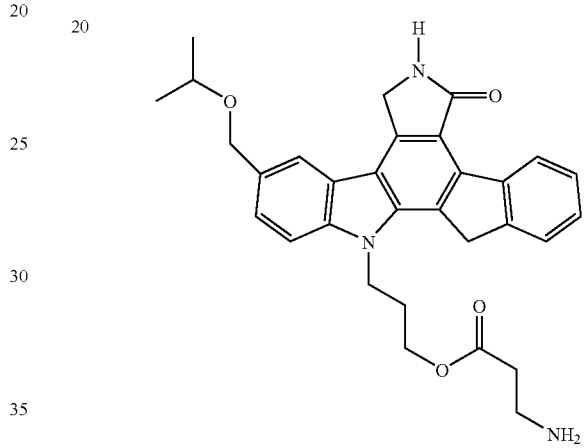 |
| 21 | 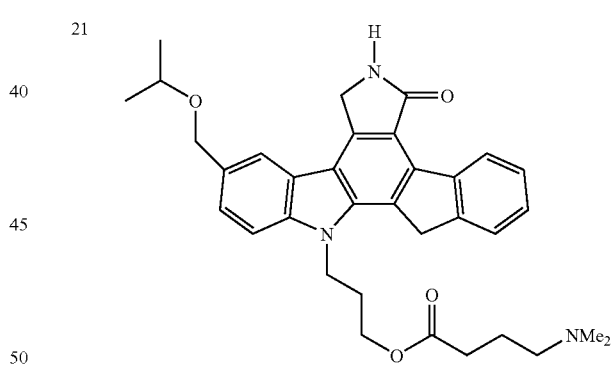 |
| 22 | 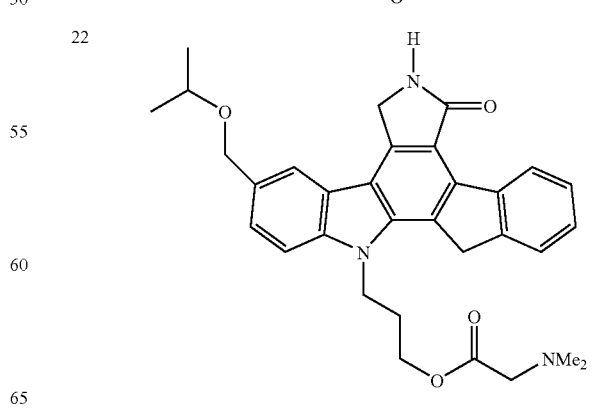 |

TABLE II-continued

| Compound | Structure |
|---|---|
| 23 | 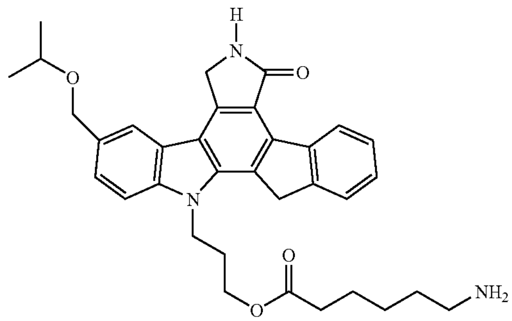 |
| 24 | 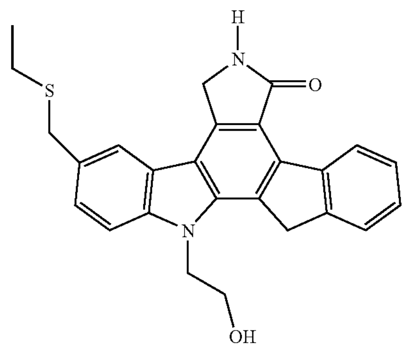 |
| 25 | 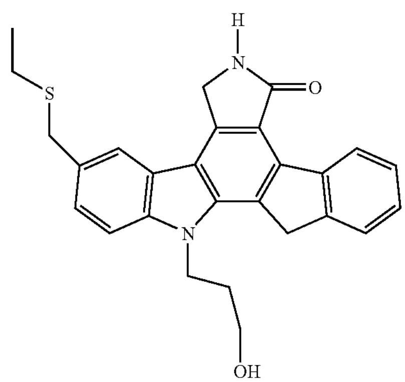 |
| 26 | 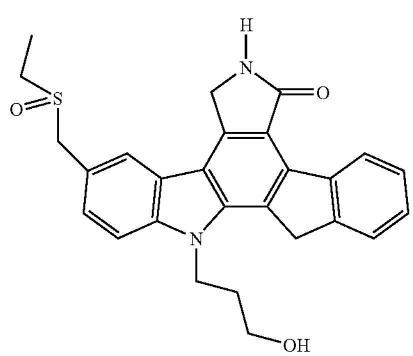 |
| 27 | |
| 28 | |
| 29 | |
| 30 | |

TABLE II-continued
| Compound | Structure |
|---|---|
| 31 | 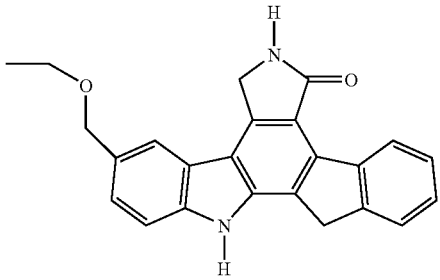 |
| 32 | 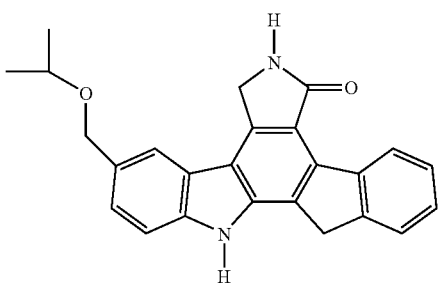 |
| 33 | 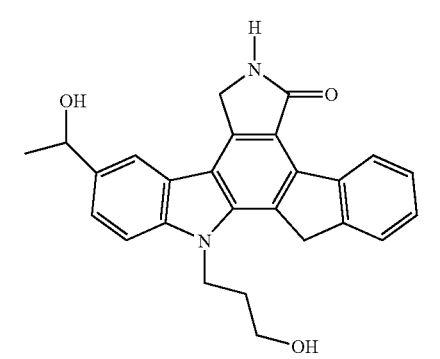 |
| 34 | 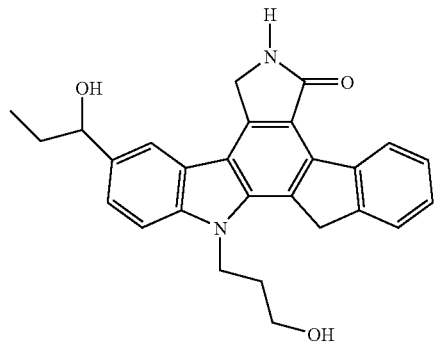 |
| 35 | 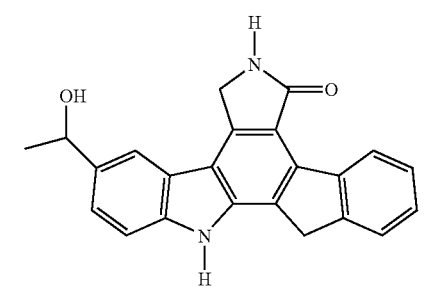 |
| 36 (+/−) | 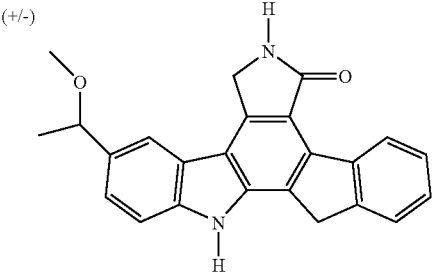 |
| 37 | 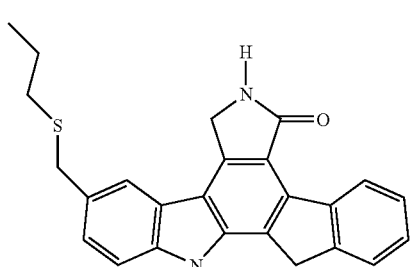 |
| 38 | 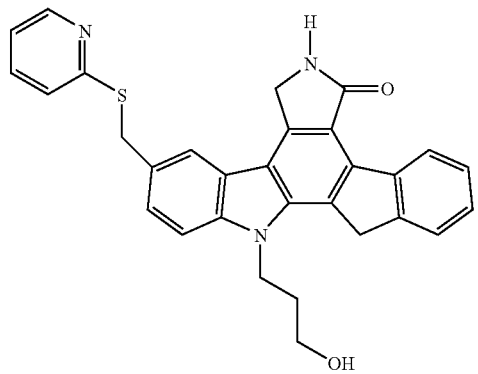 |
| 39 | 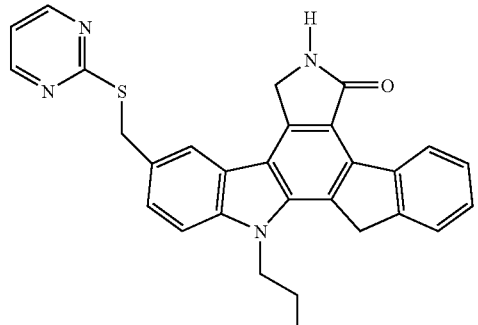 |

TABLE II-continued

| Compound | Structure |
|---|---|
| 40 | 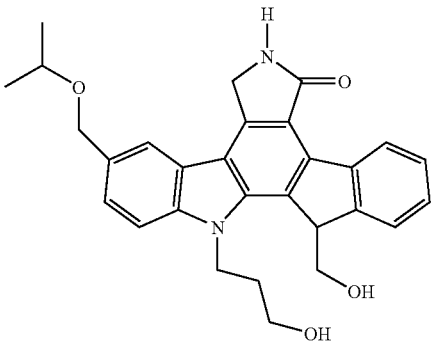 |

Particularly preferred compounds of Table II include compounds 1, 3, 4, 5, 6, 7 and 22 with compounds 3 and 22 being most preferred.

The compounds represented by Formula I and II and depicted in Tables I and II may also be referred to herein as "the compounds," "the compound(s) of the present invention," "fused pyrrolocarbazole(s)," "fused pyrrolocarbazole(s) of the present invention" and the like.

Certain compounds of U.S. Pat. No. 5,705,511 are depicted in Table IIa.

TABLE IIa

| Compound | Structure |
|---|---|
| A | 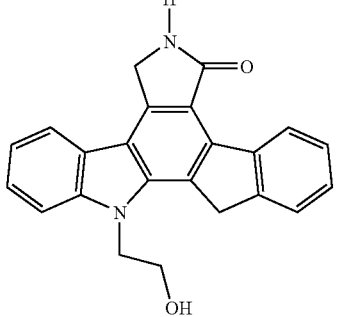 |
| B | 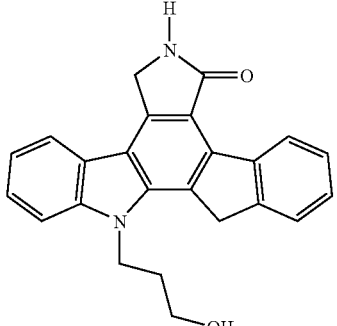 |

TABLE IIa-continued

| Compound | Structure |
|---|---|
| C | 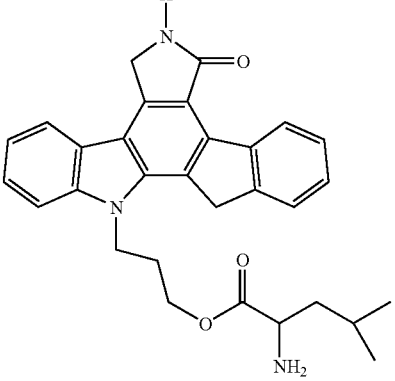 |
| D | 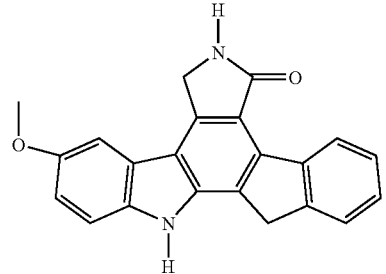 |

As used herein with reference to the definitions of $R^1$ and $R^2$, the term "amino acid" denotes a molecule containing both an amino acid group and a carboxyl group. It includes an "α-amino acid" which has its usual meaning as a carboxylic acid which bears an amino functionality on the carbon adjacent to the carboxyl group. α-Amino acids can be naturally occurring or non-naturally occurring. Amino acids also include "dipeptides" which are defined herein as two amino acids which are joined in a peptide linkage Thus constituents of dipeptides are not limited to α-amino acids, and can be any molecule containing both an amino group and a carboxyl group. Preferred are α-amino acids, dipeptides such as lysyl-β-alanine, and aminoalkanoic acids of 2–8 carbons, e.g., 3-dimethylaminobutyric acid.

Pharmaceutically acceptable salts of the fused pyrrolocarbazoles of the present invention also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients or carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches.

Accordingly, another aspect of the present invention are pharmaceutical compositions comprising a compound of the present invention optionally in admixture with one or more pharmaceutically acceptable excipients or carriers. Preferably, the pharmaceutical compositions comprise a compound of Formula II. More preferably, the pharmaceutical compositions comprise a compound of Table I or Table II.

In certain preferred pharmaceutical compositions, the composition is for inhibiting one or more of trk kinase activity, VEGFR kinase activity, PKC or PDGFR activity wherein the composition comprises a compound of Formula I, Formula II, Table I or Table II and optionally one or more pharmaceutically acceptable carrier(s). In other preferred pharmaceutical compositions the composition is for enhancing tropic factor or spinal chord ChAT activity wherein the composition comprises a compound of Formula I, Formula II, Table I or Table II and a pharmaceutically acceptable carrier.

In other preferred pharmaceutical compositions, the composition is for treating or preventing angiogenesis and angiogenic disorders such as cancer of solid tumors, endometriosis, retinopathy, diabetic retinopathy, psoriasis, hemangioblastoma, ocular disorders or macular degeneration. In other preferred pharmaceutical compositions, the composition is for treating or preventing neoplasia, rheumatoid arthritis, pulmonary fibrosis, myelofibrosis, abnormal wound healing, atherosclerosis, or restenosis. In other preferred pharmaceutical compositions, the composition is for treating or preventing neurodegenerative diseases and disorders, Alzheimer's disease, amyotrophic lateral sclerosis, Parkinson's disease, stroke, ischaemia, Huntington's disease, AIDS dementia, epilepsy, multiple sclerosis, peripheral neuropathy, chemotherapy induced peripheral neuropathy, AIDS related peripheral neuropathy, or injuries of the brain or spinal chord. In other preferred pharmaceutical compositions, the composition is for treating or preventing prostate disorders such as prostate cancer or benign prostate hyperplasia. In still other preferred pharmaceutical compositions, the composition is used for treating or preventing multiple myeloma and leukemias including, but not limited to, acute myelogenous leukemia, chronic myelogenous leukemia, acute lymphocytic leukemia, and chronic lymphocytic leukemia.

The compositions may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The compounds of the present invention can be employed as the sole active agent in a pharmaceutical or can be used in combination with other active ingredients, e.g., other growth factors which could facilitate neuronal survival or axonal regeneration in diseases or disorders or other angiogenesis or antitumor agents.

The concentrations of the compounds described herein in a therapeutic or pharmaceutical composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

In other embodiments, the present invention provides a method for inhibiting trk kinase activity comprising providing a compound of the present invention in an amount sufficient to result in effective inhibition. In a preferred embodiment, the compound of the present invention is provided to treat inflammation, for example, neurological inflammation and chronic arthritis inflammation. In another preferred embodiment, the trk kinase receptor is trk A.

In other embodiments, the present invention provides a method for treating or preventing prostate disorders which comprises administering to a host in need of such treatment or prevention a therapeutically effective amount of a compound of the present invention. In a preferred embodiment, the prostate disorder is prostate cancer or benign prostate hyperplasia.

In other embodiments, the present invention provides a method for treating or preventing angiogenic disorders where VEGFR kinase activity contributes to pathological conditions, the method comprising providing a compound of the present invention in an amount sufficient to result in the vascular endothelial growth factor receptor being contacted with an effective inhibitory amount of the compound. In another embodiment, the present invention provides a method for treating or preventing angiogenic disorders which comprises administering to a host in need of such treatment or prevention a therapeutically effective amount of a compound of the present invention. In a preferred embodiment, the angiogenic disorder is cancer of solid tumors, ocular disorders, macular degeneration, endometriosis, diabetic retinopathy, psoriasis, or hemangioblastoma.

In other embodiments, the present invention provides a method for treating or preventing disorders where PDGFR activity contributes to pathological conditions, the method comprising providing a compound of the present invention in an amount sufficient to result in the platelet derived growth factor receptor being contacted with an effective inhibitory amount of the compound. In another embodiment, the present invention provides a method for treating or preventing pathological disorders which comprises administering to a host in need of such treatment or prevention a therapeutically effective amount of a compound of the present invention. In preferred embodiments, the pathological disorder is neoplasia, rheumatoid arthritis, chronic arthritis, pulmonary fibrosis, myelofibrosis, abnormal wound healing, atherosclerosis, or restenosis.

In other embodiments, the present invention provides a method for treating disorders characterized by the aberrant activity of trophic factor responsive cells, the method comprising providing a compound of Formula I, Formula II, Table I or Table II in an amount sufficient to result in the trophic factor cell receptor being contacted with an effective activity inducing amount of the compound. In preferred embodiments, the activity of the trophic factor responsive cells is ChAT activity. In another embodiment, the present invention provides a method for treating or preventing neurodegenerative diseases and disorders, Alzheimer's disease, amyotrophic lateral sclerosis, Parkinson's disease, stroke, ischaemia, Huntington's disease, AIDS dementia, epilepsy, multiple sclerosis, peripheral neuropathy, chemotherapy induced peripheral neuropathy, AID related peripheral neuropathy or injuries of the brain or spinal chord which comprises administering to a host in need of such treatment or prevention a therapeutically effective amount of a compound of Formula I, Formula II, Table I and Table II.

As used herein, the term "effect" when used to modify the terms "function" and "survival" means a positive or negative alteration or change. An effect which is positive can be referred to herein as an "enhancement" or "enhancing" and an effect which is negative can be referred to herein as "inhibition" or "inhibiting."

As used herein, the terms "enhance" or "enhancing" when used to modify the terms "function" or "survival" means that the presence of a fused pyrrolocarbazole has a positive effect on the function and/or survival of a trophic factor responsive cell compared with a cell in the absence of the fused pyrrolocarbazole. For example, and not by way of limitation, with respect to the survival of, e.g., a cholinergic neuron, the fused pyrrolocarbazole would evidence enhancement of survival of a cholinergic neuronal population at risk of dying (due to, e.g., injury, a disease condition, a degenerative condition or natural progression) when compared to a cholinergic neuronal population not presented with such fused pyrrolocarbazole, if the treated population has a comparatively greater period of functionality than the non-treated population. As a further example, and again not by way of limitation, with respect to the function of, e.g., a sensory neuron, the fused pyrrolocarbazole would evidence enhancement of the function (e.g. neurite extension) of a sensory neuronal population when compared to a sensory neuronal population not presented with such fused pyrrolocarbazole, if the neurite extension of the treated population is comparatively greater than the neurite extension of the non-treated population.

As used herein, "inhibit" and "inhibition" mean that a specified response of a designated material (e.g., enzymatic activity) is comparatively decreased in the presence of a fused pyrrolocarbazole of the present invention.

As used herein the term "neuron," "cell of neuronal lineage" and "neuronal cell" includes, but is not limited to, a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain and spinal cord neurons. As used herein, the phrase "sensory neuron" includes neurons responsive to environmental cues (e.g., temperature, movement) from, e.g., skin, muscle and joints; exemplary is a neuron from the DRG.

As used herein a "trophic factor" is a molecule that directly or indirectly affects the survival or function of a trophic factor responsive cell. Exemplary trophic factors include Ciliary Neurotrophic Factor (CNTF), basic Fibroblast Growth Factor (bFGF), insulin and insulin-like growth factors (e.g., IGF-I, IGF-II, IGF-III), interferons, interleukins, cytokines, and the neurotrophins, including Nerve Growth Factor (NGF), Neurotrophin-3 (NT-3), Neurotrophin-4/5 (NT-4/5) and Brain Derived Neurotrophic Factor (BDNF).

A "trophic factor-responsive cell," as defined herein, is a cell which includes a receptor to which a trophic factor can specifically bind; examples include neurons (e.g., cholinergic and sensory neurons) and non-neuronal cells (e.g., monocytes and neoplastic cells).

As used herein, "trophic factor activity" and "trophic factor induced activity" are defined as any response which directly or indirectly results from the binding of a trophic factor (e.g., NGF) to a cell comprising a trophic factor receptor (e.g., neuron comprising of a trk). In the case of, e.g., NGF binding with trk, an exemplary response would include autophosphorylation of trk tyrosine residues leading to increased ChAT activity which results in enhanced neuron survival, and/or function.

As used in the phrases "trophic factor activity" and "trophic factor-induced activity," the term "trophic factor" includes both endogenous and exogenous trophic factors, where "endogenous" refers to a trophic factor normally present and "exogenous" refers to a trophic factor added to a system. As defined, "trophic factor induced activity" includes activity induced by (1) endogenous trophic factors; (2) exogenous trophic factors; and (3) a combination of endogenous and exogenous trophic factors.

As used herein, the term "trk" refers to the family of high affinity neurotrophin receptors presently comprising trk A, trk B and trk C, and other membrane associated proteins to which a neurotrophin can bind.

As used herein the phrase "hyperproliferative state" in reference to the term "cells" means cells whose unregulated and/or abnormal growth can lead to the development of an unwanted condition, for example, a cancerous condition or a psoriatic condition.

As used herein, "cancer" and "cancerous" refer to any malignant proliferation of cells in a mammal. Examples include prostate, benign prostate hyperplasia, ovarian, breast and other recognized cancers. As used herein the term "psoriasis" and "psoriatic condition" refer to disorders involving keratinocyte hyperproliferation, inflammatory cell infiltration and cytokine alteration.

As used herein, the phrase "at risk of dying" in conjunction with a biological material, e.g., a cell such as a neuron, means a state or condition which negatively impacts the biological material such that the material has an increased likelihood of dying due to such state or condition. For example, compounds disclosed herein can "rescue" or enhance the survival of motoneurons which are naturally at risk of dying in an in ovo model of programmed cell death. Similarly, for example, a neuron may be at risk of dying due to the natural aging process which occasions the death of a neuron, or due to an injury, such as a trauma to the head, which may be such that neurons and/or glia, for example, impacted by such trauma may be at risk of dying. Further, for example, a neuron may be at risk of dying due to a disease state or condition, as in the case of neurons at risk of dying as occasioned by the disease ALS. Thus, by enhancing the survival of a cell at risk of dying by use of a compound of the claimed invention is meant that such compound decreases or prevents the risk of the death of the cell.

As used herein the term "contacting" means directly or indirectly causing placement together of moieties, such that the moieties directly or indirectly come into physical association with each other, whereby a desired outcome is achieved. Thus, as used herein, one can "contact" a target cell with a compound as disclosed herein even though the compound and cell do not necessarily physically join together (as, for example, is the case where a ligand and a receptor physically join together), as long as the desired outcome is achieved (e.g., enhancement of the survival of the cell). Contacting thus includes acts such as placing moieties together in a container (e.g., adding a compound as disclosed herein to a container comprising cells for in vitro studies) as well as administration of the compound to a target entity (e.g., injecting a compound as disclosed herein into a laboratory animal for in vivo testing, or into a human for therapy or treatment purposes).

As used herein, "prodrug" is intended to include any covalently bonded carriers which release the active parent drug as a compound of the present invention in vivo when such prodrug is administered to a mammalian subject. Since prodrugs are known to enhance numerous desirable qualities of pharmaceuticals (e.g., solubility, bioavailability, manufacturing, etc.) the compounds of the present invention may be delivered in prodrug form. Thus, the present invention contemplates prodrugs of the compounds of the present invention, compositions containing the same, and methods of treating diseases and disorders with such prodrugs. Prodrugs of a compound of the present invention, for example Formula I, may be prepared by modifying functional groups present in the compound in such a way that the modifications are cleaved, either in routine manipulation or in vivo, to the parent compound. Accordingly, prodrugs include, for example, compounds of the present invention wherein a hydroxy, amino, or carboxy group is bonded to any group that, when the prodrug is administered to a mammalian subject, cleaves to form a free hydroxyl, free amino, or carboxylic acid, respectively. Examples include, but are not limited to, the residue of an amino acid after the hydroxyl group of the carboxyl group is removed acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The fused pyrrolocarbazoles of the present invention have important functional pharmacological activities which find utility in a variety of settings, including both research and therapeutic arenas. For ease of presentation, and in order not to limit the range of utilities for which these compounds can be characterized, we generally describe the activities of the fused pyrrolocarbazoles as follows:

1. Inhibition of enzymatic activity
2. Effect on the function and/or survival of trophic factor responsive cells
3. Inhibition of inflammation-associated responses
4. Inhibition of cell growth associated with hyperproliferative states
5. Inhibition of developmentally programmed motoneuron death Inhibition of enzymatic activity can be determined using, for example, VEGFR inhibition (e.g., VEGFR2 inhibition), MLK inhibition (e.g., MLK1, MLK2 or MLK3 inhibition), PDGFR kinase inhibition, NGF-stimulated trk phosphorylation, PKC inhibition, or trk tyrosine kinase inhibition assays. Effect on the function and/or survival of trophic factor responsive cells, e.g., cells of a neuronal lineage, can be established using any of the following assays: (1) cultured spinal cord choline acetyltransferase ("ChAT") assay; (2) cultured dorsal root ganglion ("DRG") neurite extension assay; (3) cultured basal forebrain neuron ("BFN") ChAT activity assay. Inhibition of inflammation-associated response can be established using an indoleamine 2,3-dioxygenase ("IDO") mRNA assay. Inhibition of cell growth associated with hyperproliferative states can be determined by measuring the growth of cell lines of interest, such as an AT2 line in the case of prostate cancer. Inhibition of developmentally programmed motoneuron death can be assessed in ovo using embryonic chick somatic motoneurons, which cells undergo naturally occurring death between embryonic days 6 and 10, and analyzing inhibition of such naturally occurring cell death as mediated by the compounds disclosed herein.

The inhibition of enzymatic activity by the fused pyrrolocarbazole compounds of the present invention can be determined using, for example, the following assays:

VEGFR Inhibition Assay
MLK Inhibition Assay
PKC Activity Inhibition Assay
trkA Tyrosine Kinase Activity Inhibition Assay
Inhibition of NGF-stimulated trk phosphorylation in a whole cell preparation
Platelet Derived Growth Factor Receptor (PDGFR) inhibition assay Particularly, inhibition of the Vascular Endothelial Growth Factor Receptor (VEGFR) implies utility in, for example, diseases where angiogenesis plays important roles, such as cancer of solid tumors, endometriosis, diabetic retinopathy, psoriasis, hemangioblastoma, as well as other ocular diseases and cancers. Inhibition of MLK implies utility in, for example, neurological diseases. Inhibition of trk implies utility in, for example, diseases of the prostate such as prostate cancer and benign prostate hyperplasia, and treatment of inflammatory pain. Inhibition of the Platelet Derived Growth Factor Receptor (PDGFR) implies utility in, for example, various forms of neoplasia, rheumatoid arthritis, pulmonary fibrosis, myelofibrosis, abnormal wound healing, diseases with cardiovascular end points, such as atherosclerosis, restenosis, post-angioplasty restenosis, and the like.

Fused pyrrolocarbazoles have also been shown to have positive effects on the function and survival of trophic factor responsive cells by promoting the survival of neurons. With respect to the survival of a cholinergic neuron, for example, the compound may preserve the survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population.

A variety of neurological disorders are characterized by neuronal cells which are dying, injured, functionally compromised, undergoing axonal degeneration, at risk of dying, etc. These disorders include, but are not limited to, neurological diseases and disorders, Alzheimer's disease; motor neuron disorders (e.g. amyotrophic lateral sclerosis); Parkinson's disease; cerebrovascular disorders (e.g., stroke, ischaemia); Huntington's disease; AIDS dementia; epilepsy; multiple sclerosis; peripheral neuropathies (e.g., those affecting DRG neurons in chemotherapy-associated peripheral neuropathy) including diabetic neuropathy and AIDS related peripheral neuropathy; disorders induced by excitatory amino acids; and disorders associated with concussive or penetrating injuries of the brain or spinal cord.

The compounds are not only useful for enhancing trophic factor-induced activities of trophic responsive cells, e.g., cholinergic neurons, but also may function as survival promoting agents for other neuronal cell types, e.g., dopaminergic or glutamatergic. Growth factor may regulate survival of neurons by signaling cascades downstream of the small GTP binding proteins ras, rac, and cdc42 (Denhardt, D. T., Biochem. J., 1996, 318, 729). Specifically, activation of ras leads to phosphorylation and activation of extracellular receptor-activated kinase (ERK), which has been linked to biological growth and differentiation processes.

Stimulation of rac/cdc42 leads to an increase in activation of JNK and p38, responses that are associated with stress, apoptosis, and inflammation. Although growth factor responses are primarily via the ERK pathway, affecting these latter processes may lead to alternative mechanisms of neuronal survival which may mimic growth factor enhancing survival properties (Xia et al., Science, 1995, 270, 1326). The compounds of the present invention may also function as survival promoting agents for neuronal and non-neuronal cells by mechanisms related to, but also distinct from, growth factor mediated survival, for example, inhibition of the JNK and p38 MAPK pathways which may lead to survival by inhibition of apoptotic cell death processes.

The present compounds are also useful in the treatment of disorders associated with decreased ChAT activity or the death, injury to spinal cord motoneurons, and also have utility in, for example, diseases associated with apoptotic cell death of the central and peripheral nervous system, immune system and in inflammatory diseases. ChAT catalyzes the synthesis of the neurotransmitter acetylcholine, and it is considered an enzymatic marker for a functional cholinergic neuron. A functional neuron is also capable of survival. Neuron survival is assayed by quantitation of the specific uptake and enzymatic conversion of a dye (e.g., calcein AM) by living neurons. The compounds described herein may also find utility in the treatment of disease states involving malignant cell proliferation, such as many cancers.

Because of their varied utilities, the properties of isomeric fused pyrrolocarbazoles and isoindolones may be exploited in other settings, such as research. For example, the compounds can be used in the development of in vitro models of neuronal cell survival, function, identification, or for the screening of other synthetic compounds which have activities similar to that of the of isomeric fused pyrrolocarbazole and isoindolone compounds. Thus, the compounds provided by this invention are useful as standard or reference compounds for use in tests or assays for determining the activity of an agent in a pharmaceutical research program.

The compounds can also be utilized to investigate, define and determine molecular targets associated with functional responses. For example, by radiolabelling an isomeric fused pyrrolocarbazole or isoindolone compound associated with a specific cellular function (e.g., mitogenesis), the target entity to which the derivative binds can be identified, isolated, and purified for characterization. By way of further illustration, compounds may be used in the development of assays and models for further enhancement of the understanding of the roles that inhibition of serine/threonine or tyrosine protein kinase (e.g., PKC, trk tyrosine kinase) play in the mechanistic aspects of the associated disorders and diseases. Thus, the compounds of the present invention are useful as diagnostic reagents in diagnostic assays, such as the assays described herein.

The results obtained in the VEGFR and MLK assays are set forth below. Other assays are described in more detail as well. They are not intended, nor are they to be construed, as limiting the scope of the disclosure. Certain abbreviations used to delineate the results below are defined as follows: "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer.

Synthesis

The present invention also provides a method for preparing the fused pyrrolocarbazoles of the present invention. The compounds of the present invention may be prepared in a number of ways well known to those skilled in the art. The compounds can be synthesized, for example, by the methods described in the Schemes below, or variations thereon as appreciated by the skilled artisan. The appropriate modifications and substitutions being readily apparent and well known or readily obtainable from the scientific literature to those skilled in the art. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

As will be readily understood, functional groups present on the compounds of the present invention may contain protecting groups. For example, the amino acid side chain substituents of the compounds can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., "Protective Groups in Organic Synthesis" 2d. Ed., Wiley & Sons, 1991.

Scheme 1
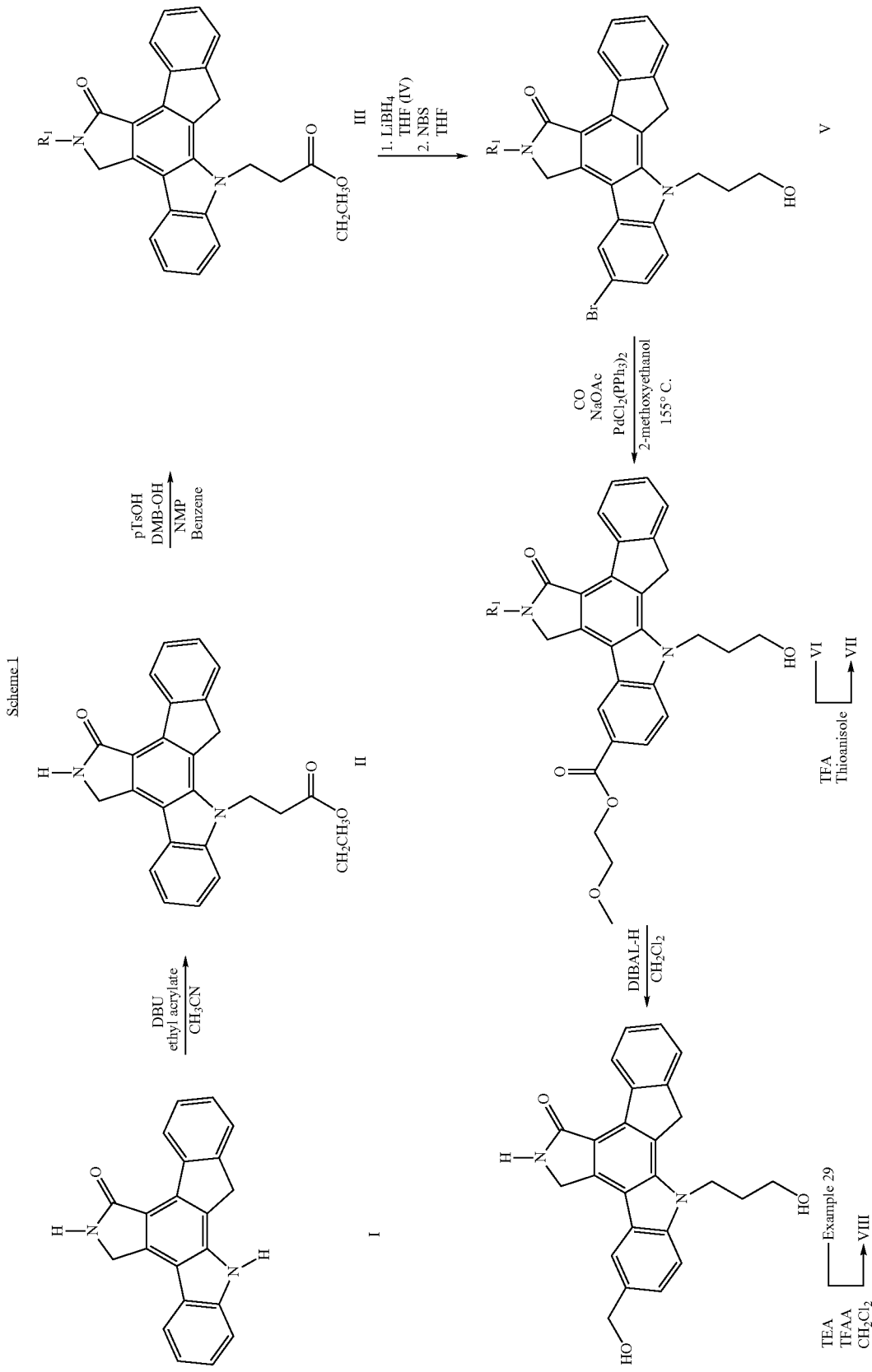

Scheme 2
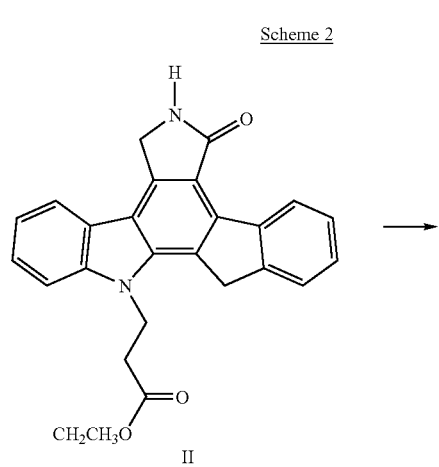
II
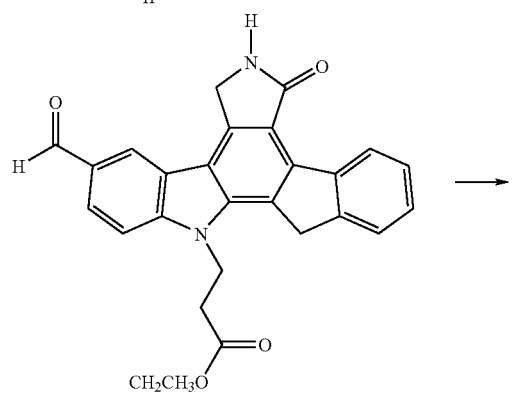
X
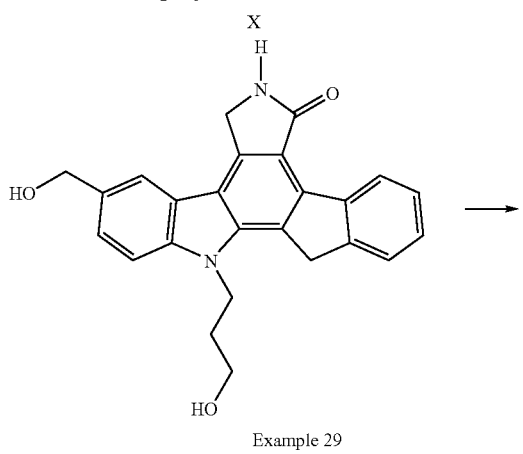
Example 29
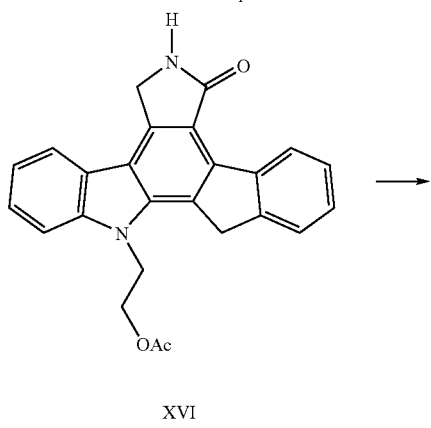
XVI
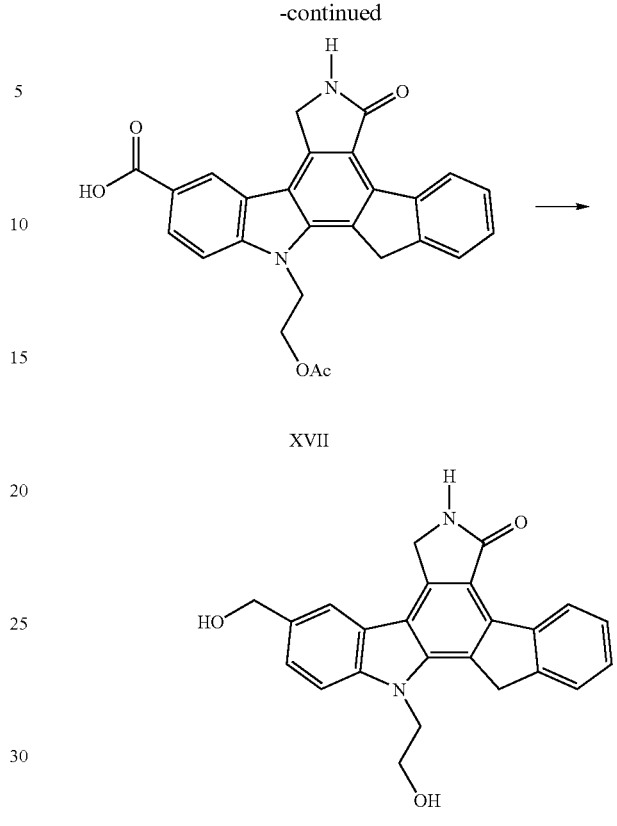
XVII
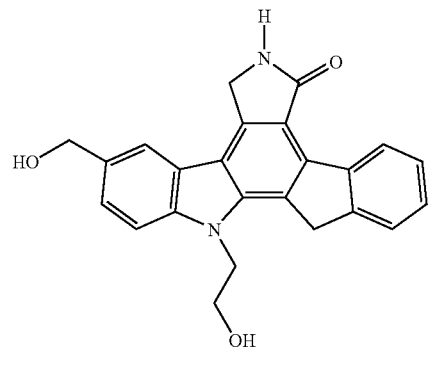
Example 28
Scheme 3
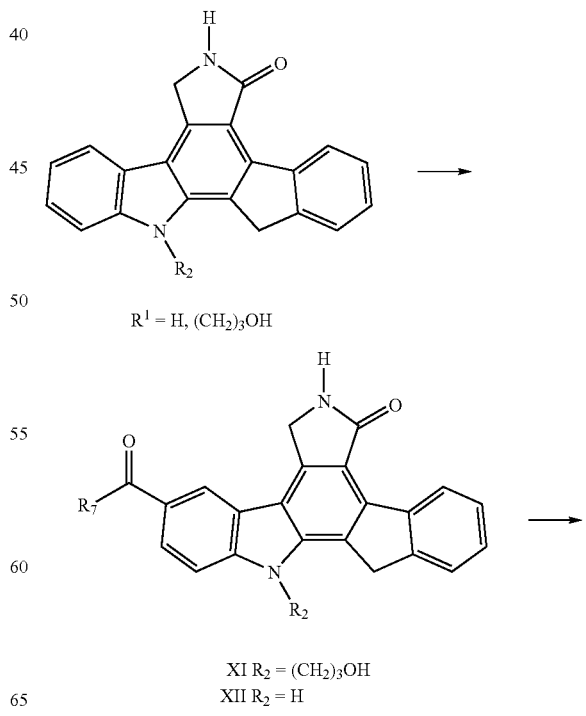
$R^1$ = H, (CH$_2$)$_3$OH
XI R$_2$ = (CH$_2$)$_3$OH
XII R$_2$ = H -continued
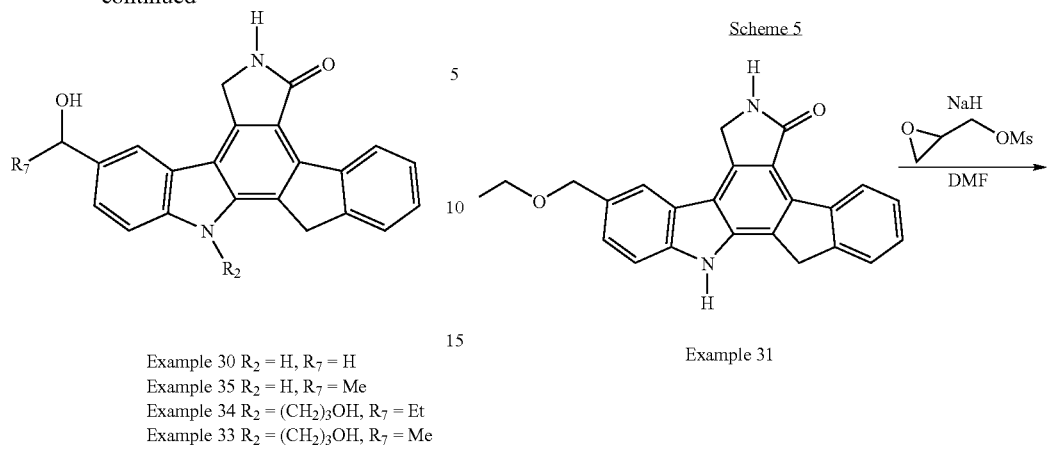
Example 30 R₂ = H, R₇ = H
Example 35 R₂ = H, R₇ = Me
Example 34 R₂ = (CH₂)₃OH, R₇ = Et
Example 33 R₂ = (CH₂)₃OH, R₇ = Me
Scheme 5
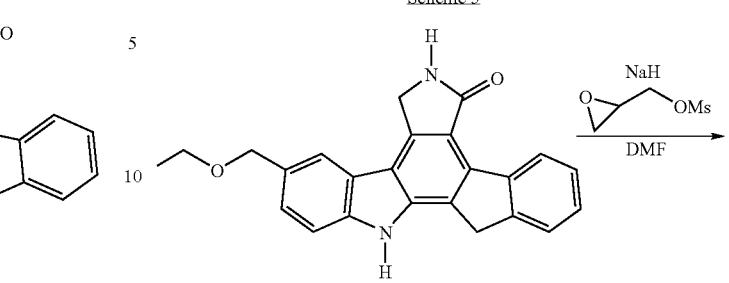
Example 31
Scheme 4
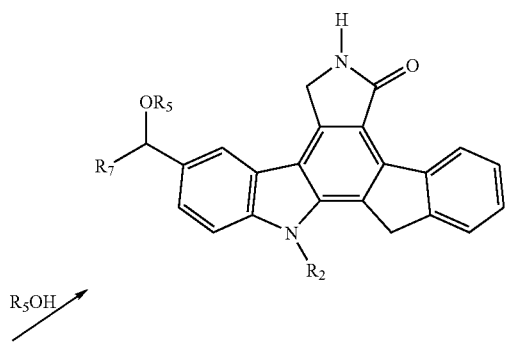
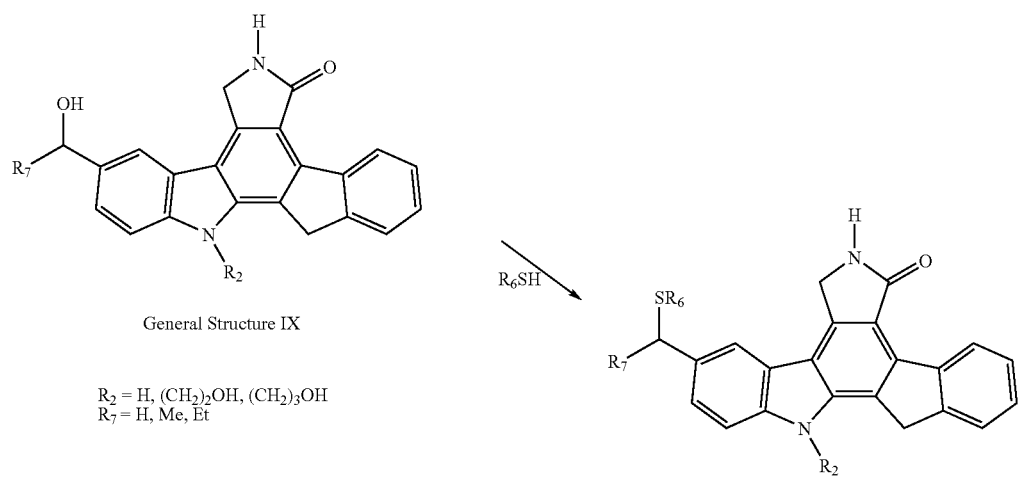
General Structure IX
R₂ = H, (CH₂)₂OH, (CH₂)₃OH
R₇ = H, Me, Et -continued
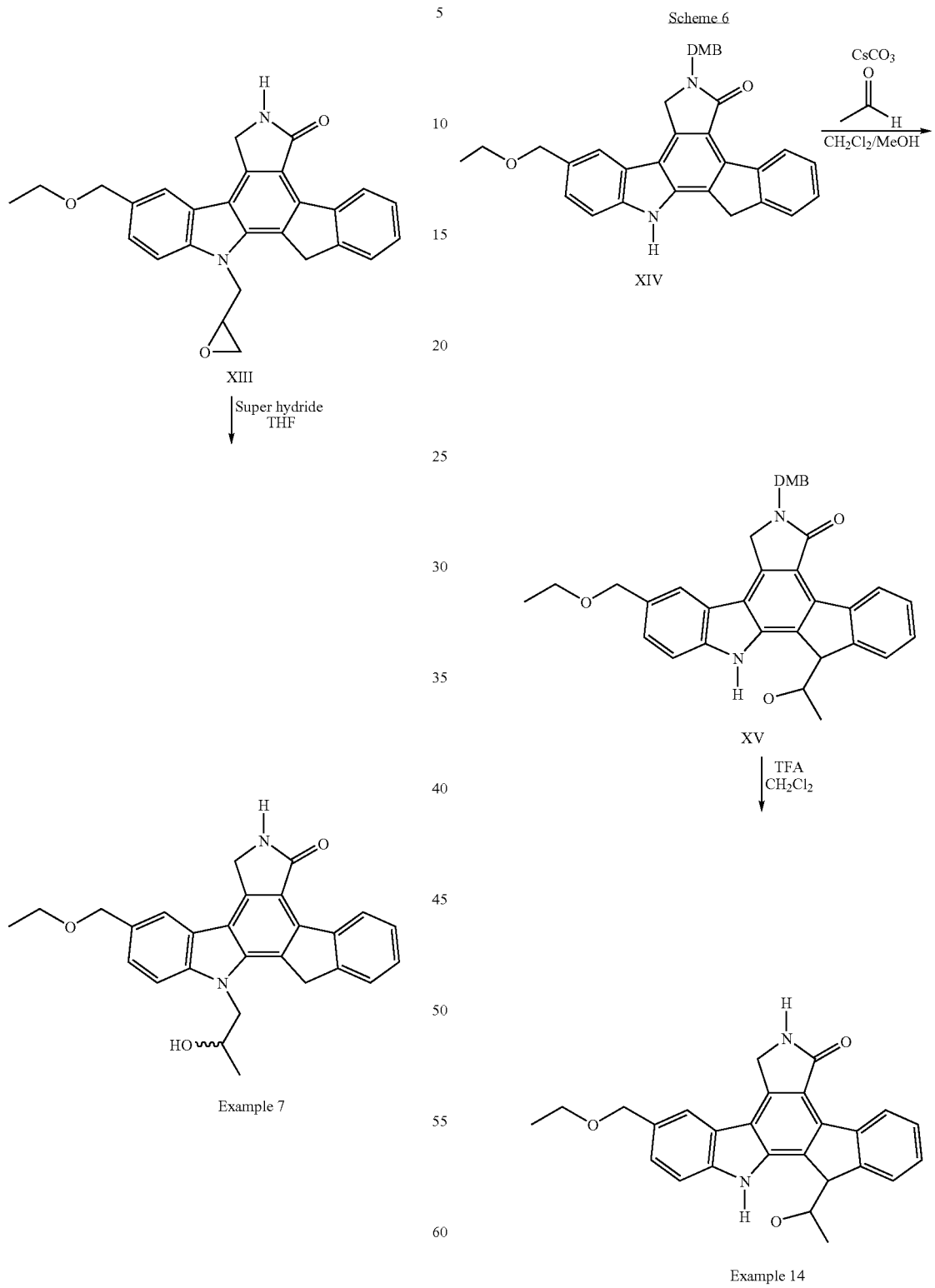

Scheme 7
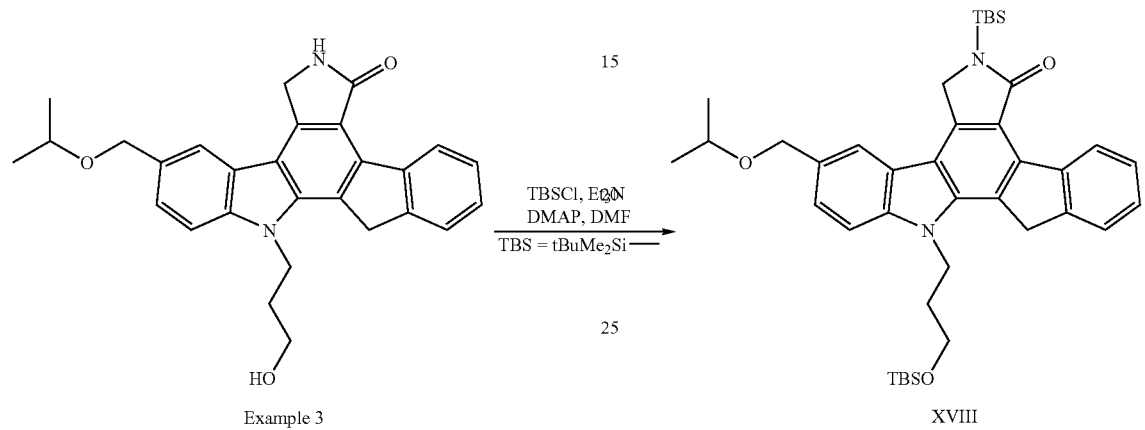

Scheme 8

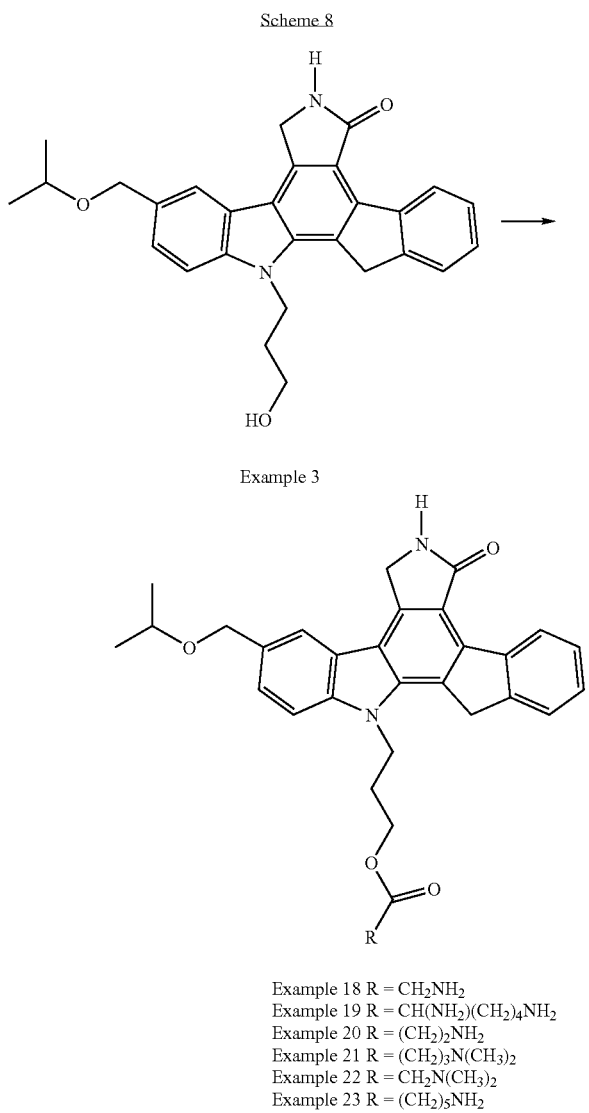

Example 3

Example 18 R = CH₂NH₂
Example 19 R = CH(NH₂)(CH₂)₄NH₂
Example 20 R = (CH₂)₂NH₂
Example 21 R = (CH₂)₃N(CH₃)₂
Example 22 R = CH₂N(CH₃)₂
Example 23 R = (CH₂)₅NH₂

Description of Synthesis

Compounds A and B were prepared by alkylation's of indole I with 2-bromoethyl benzyl ether (A) or with 3-bromopropyl benzyl ether (B) using NaH in DMF, followed by debenzylation (Pd(OH)₂/H₂) as described in U.S. Pat. No. 5,705,511. Reference compound C was prepared by coupling B with Boc-leucine followed by deprotection of the BOC group using standard procedures know to those skilled in the art of organic synthesis. Compound B may also be prepared by reduction of ester IV with reducing agents such as LiBH₄ followed by removal of the benzhydrol protecting group. The routes to prepare the benzyl ethers and thiol ethers are outlined in the schemes. Two methods are used to prepare the 3-hydroxymethyl intermediates 28–30, 33–35. Scheme 1 (Method A) delineates a carbonylation route while scheme 2 (method B) utilizes a formylation method. In scheme 1 Michael reaction of I with ethyl acrylate and a base such as DBU produces II, followed by lactam nitrogen protection with dimethoxybenzhydrol to III. Reduction of the ethyl ester using reducing agents such as lithium borohydride, followed by bromination with N-bromo succinimide provided intermediate V in good overall yield. Palladium catalyzed carbonylation of V in methoxyethanol gave the methoxyethoxy ester VI. After deprotection to VII, the ester could be reduced with reducing agents, for example diisobutylaluminum hydride (DIBAL-H) to give the diol 29. The formylation route to the hydroxymethyl compounds (method B, scheme 2) uses for example, HMTA in TFA or α,α-dichloromethyl methyl ether and a Lewis acid. The aldehydes may be reduced to hydroxymethyl compounds using reducing agents such as sodium borohydride or diisobutylaluminum hydride. The methyl ether or thio ether examples may be prepared using a general procedure outlined in scheme 4. In one approach, for example, the diol 29 may be converted to a tri-trifluoroacetate intermediate with trifluoroacetic anhydride and a base such as triethylamine, followed by treating this intermediate with an appropriate alkyl alcohol or alkyl thiol to give the benzyl ether (1–25, 27, 31, 32, 36–40) directly. In certain cases the trifluoroacetate ester of the primary alcohol may be isolated. In these examples the alcohol may be isolated by treatment of the trifluoroacetate with a base such as lithium hydroxide. In another approach, the ethers and thio ethers may be prepared by reacting a diol, for example 28 or 29, with an alcohol and an acid catalyst, such as p-toluene sulfonic acid or camphor-sulfonic acid in a solvent, for example, methylene chloride, toluene or 1,2-dichloroethane.

Alcohols 33–35 were used to prepare ether examples 10–13, 15, 16 and 36. Examples 33–35 were prepared from ketones XI and XII as outlined in scheme 3. The ethers and thio ethers were prepared using the procedures described previously and outlined in scheme 4.

Example 7 was prepared as shown in scheme 5. Example 31 was alkylated with mesyl glycidol to give compound XIII. Reduction with triethylborohydride in THF produced example secondary alcohol 7. Example 14 was prepared (scheme 6) by treatment of compound XIV with cesium carbonate and acetaldehyde in methylene chloride/methanol. Example 40 was prepared as shown in scheme 7. The Di-TBS protected XVIII, was alkylated with paraformaldehyde using triton B/pyridine, followed by deprotection using TMSCl to give example 40. The amino acid esters, example 18–23 were prepared from example 3 and the corresponding carboxylic acid using standard coupling reaction known to those skilled in the art of organic synthesis.

Other features of the invention will become apparent in the course of the following descriptions of exemplary embodiments. These examples are given for illustration of the invention and are not intended to be limiting thereof.

EXAMPLES

Certain abbreviations used herein are defined as follows: "° C." for degrees Celsius, "d" for doublet, "dd" for doublet of doublets, "t" for triplet, "m" for multiplet, "eq" for equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy.

Preparation of Compound II:

To a suspension of I (8.0 g, 0.258 mols) in acetonitrile (300 mL) at room temperature under nitrogen was added ethyl acrylate (4.19 mL, 0.387 mols) followed by 1,8-diazabicyclo[5.4.0]undec-7-ene (DBU) (1.93 mL, 0.013 mols). After addition of DBU, the reaction changed colors from orange to green. The reaction mixture was heated to reflux overnight. The mixture remained heterogeneous throughout the course of the reaction and became dark in color. A small aliquot was removed after 18 h and the solid was collected by filtration. $^1$H NMR of the sample showed no starting material remaining. The reaction mixture was cooled to room temperature and the solid was collected by filtration. The solid was washed several times with cold acetonitrile and dried in vacuo at 55° C. to yield a light orange solid (5.4 g, 78% yield). $^1$H NMR (DMSO-d6, 300 MHz): δ 9.72 (t, 3H, J=6.8), 2.87 (m, 2H), 3.89 (q, 2H, J=6.8), 4.49 (s, 2H), 4.88 (s, 2H), 4.92 (m, 2H), 7.29–7.48 (m, 3H), 7.50–7.73 (m, 3H), 7.96 (d, 1H, J 7.33), 8.56 (s, 1H), 9.47 (d, 1H, J=7.33).

Preparation of Compound III:

To a suspension of II (5.62 g, 0.0137 mols) in benzene (300 mL) and N-methylpyrrolidine (NMP) (60 mL) at room temperature under nitrogen was added p-toluenesulfonic acid monohydrate (2.48 g, 0.013 mols) and 4,4'-dimethoxybenzhydrol (3.19 g, 0.013 mols). The contents of the flask were heated to reflux for 8 h. After 45 min., the initially heterogeneous reaction mixture became homogeneous. The reaction mixture was cooled to room temperature, diluted with ethyl acetate (300 mL) and washed with a saturated bicarbonate solution, water, and brine. The organic layer was dried over magnesium sulfate, filtered and concentrated in vacuo to an orange solid (8.31 g, 95% yield). $^1$H NMR (CDCl$_3$, 300 MHz): δ 1.18 (t, 3H, J=7.1), 2.84 (m, 2H), 3.80 (6H, s), 4.12 (q, 2H, J=7.1), 4.38 (s, 2H), 4.72 (2H, s), 4.94 (m, 2H), 6.90 (d, 4H, J=8.5), 6.955 (s, 1H), 7.26 (d, 4H, J=8.5), 7.34–7.49 (m, 5H), 7.61 (d, 1H, J=7.4), 7.69 (d, 1H, J=7.7), 9.65 (d, 1H, J=7.8).

Preparation of Compound IV:

To a stirred solution of III (7.8 g, 0.0122 mols) in THF (480 mL) and methanol (93 mL) was added lithium borohydride (18.9 mL of a 2.0 M soln, 0.0379 mols) dropwise. The reaction mixture was initially homogeneous, however, as the reaction proceeded, the mixture became heterogeneous. When all of the starting material had been consumed, the reaction mixture was cooled in an ice bath and carefully quenched with 2N HCl (60 mL). The reaction mixture became homogeneous and light orange in color. Water (750 mL) was added to the mixture and a milky white precipitate formed. The precipitate was collected by filtration and dried in vacuo to give a fluffy white solid (7.2 g, 99% yield). $^1$H NMR (DMSO-d$_6$, 300 MHz): δ 1.93 (m, 2H), 3.66 (m, 2H), 3.71 (s, 6H), 4.55 (s, 2H), 4.73 (m, 2H), 4.79 (s, 2H), 6.70 (s, 1H), 6.93 (d, 4H, J=8.44), 7.22 (d, 4H, J=8.4), 7.26 (m, 1H), 7.34–7.46 (m, 2H), 7.49 (m, 1H), 7.65 (d, 1H, J=7.01), 7.70 (d, 1H, J=8.26), 7.86 (d, 1H, J=7.82), 9.49 (d, 1H, J=7.49).

Preparation of Compound V:

To a suspension of IV (2.02 g, 0.0034 mols) in THF (131 mL) at room temperature under nitrogen was added N-bromosuccinimide (0.63 g, 0.0036 mols) in one portion. The reaction mixture stirred at room temperature overnight. The reaction solvent was removed in vacuo leaving a pale yellow solid. The solid was triturated with cold methanol and collected by filtration. The solid was dried in vacuo to give a pale yellow solid (1.98, 87% yield). $^1$H NMR (DMSO-d$_6$, 300 MHz) δ 1.91 (m, 2H), 3.44 (m, 2H), 3.72 (s, 6H), 4.53 (s, 2H), 474 (m, 2H), 4.87 (s, 2H), 6.71 (s, 1H), 6.93 (d, 4H, J=8.14), 7.25 (d, 4H, J=8.1), 7.37 (m, 2H), 7.59–7.69 (m, 3H), 8.08 (s, 1H), 9.50 (d, 1H, J=7.01).

Preparation of Compound VI:

In a Schlenk tube was placed V (0.79 g, 0.0017 mols) in methoxyethanol (25 mL) followed by sodium acetate (0.57 g, 0.00702 mols) and dichlorobis(triphenylphosphine)-palladium(II) (0.082 g, 0.000117 mols). The tube was evacuated and filled with carbon monoxide. The reaction mixture was heated in the sealed tube at 155° C. in an oil bath for 3 h. The reaction was cooled to room temperature and additional carbon monoxide was added. The mixture was reheated to 150° C. for another 3 h. Additional CO and PdCl$_2$(PPh$_3$)$_2$ were added and the mixture heated for 4 h. The reaction mixture was diluted with methylene chloride and flushed through a pad of celite. The filtrate was concentrated in vacuo to a residue, which was dissolved in ethyl acetate and washed with water. The organic layer was dried over magnesium sulfate, filtered, and concentrated in vacuo to a solid which was triturated with ethyl ether and collected by filtration to yield a light orange solid (0.7 g, 85% yield). $^1$H NMR (CDCl$_3$, 300 MHz): δ 2.14 (m, 2H), 3.44 (s, 3H), 3.67–3.78 (m, 4H), 3.81 (s, 6H), 4.44 (s, 2H), 4.51 (m, 2H), 4.81 (m, 4H), 6.91 (d, 4H, J=8.53), 6.98 (s, 1H), 7.28 (d, 4H, 8.6), 7.34–7.7.61 (m, 4H), 8.21 (d, 1H, J=8.32), 8.42 (s, 1H), 9.67 (d, 1H, J=7.61).

Preparation of Compound VII:

To a solution of VI (0.96 g, 0.00138 mols) in CH$_2$Cl$_2$ (30 mL) at 0° C. under nitrogen was added thioanisole (3.2 mL, 0.110 mols) followed by trifluoroacetic acid (TFA) (8.5 mL, 0.0276 mols). Upon addition of TFA, the reaction mixture turned red in color. The mixture stirred at 0° C. for 1 h and was warmed to room temperature overnight. The reaction solvent was removed in vacuo leaving a dark red oil. Ethyl ether was added to the oil and the reaction mixture turned yellow in color and a tan solid precipitated out of solution. The solid was collected by filtration (0.6 g, 92% yield). $^1$H NMR (DMSO-d$_6$, 300 MHz): δ 2.29 (m, 2H), 3.3 (m, 2H), 3.73 (m, 2H), 4.45 (m, 2H), 4.54 (m, 3H), 4.82 (m, 2H), 4.99 (s, 2H), 7.40 (m, 2H), 7.58 (d, 1H), 7.85 (d, 1H), 8.13 (d, 1H), 8.52 (s, 1H), 8.6 (s, 1H), 9.49 (d, 1H).

Example 29 (Method A)

To a stirred suspension of VII (4.4 g, 0.00935 mols) in CHCl$_2$ (220 mL) at 0° C. under nitrogen was added DIBAL-H slowly dropwise. The reaction gradually became homogeneous. The orange-colored reaction mixture stirred at 0° C. for 1 h then was warmed to room temperature and was stirred for 6 h. The mixture was cooled to 0° C. in an ice bath and water (50 mL) was added extremely slowly initially. Vigorous evolution of gas was observed. An aqueous solution of NaOH (1M, 300 mL) was added and the reaction mixture-stirred at room temperature for 1 h. A precipitate formed and was collected by filtration to yield a tan solid (3.6 g, 96%). $^1$H NMR (DMSO-d$_6$, 300 MHz): δ 1.92 (m, 2H), 3.46 (m, 2H), 4.50 (s, 2H), 4.65 (s, 2H), 4.71 (m, 2H), 4.88 (s, 2H), 7.32–7.39 (m, 2H), 7.47 (d, 1H, J=8.34), 7.65 (m, 2H), 7.89 (s, 1H), 8.53 (s, 1H), 9.46 (d, 1H, J=7.44).

Preparation of Compound X:

To a stirred solution of II (2.77 g, 6.75 mmols) in methylene chloride/toluene (3:1, 30/10 mLs) was added tin chloride (15 eq.) and α,α-dichloromethylmethyl ether (20 eq.). The mixture changed colors from orange to dark green. The reaction mixture was monitored by HPLC for disappearance of starting material. The mixture was cooled to 0° C. and quenched with aq. HCl. The material was transferred to a round-bottomed flask and concentrated in vacuo to a green-brown oil. Additional HCl and ethyl acetate were added and the material was again concentrated in vacuo. A brownish-pink solid precipitated out of solution. The solid was triturated with hexanes and the solvent decanted. This procedure was repeated 5 times. The solid was collected by filtration and dried to yield a light pinkish-brown solid 2.65 g (90% yield). MS (ESI): m/e 439 (M+H)$^+$, $^1$H NMR (DMSO-d6, 300 MHz): δ 1.00 (t, 3H), 2.94 (m, 2H), 3.93 (q, 2H), 4.50 (s, 2H), 4.97 (m, 4H), 7.37 (m, 2H), 7.65 (d, 1H), 7.96 (d, 1H), 8.03 (d, 1H), 8.52 (s, 1H), 8.67 (s, 1H), 9.48 (d, 1H), 10.49 (s, 1H).

Example 29 (Method B)

To a suspension of compound X (2.37 g, 0.005 mol) in THF (50 mL) at 0° C. under nitrogen was added lithium borohydride (10 eq.). The light brown mixture stirred at room temperature for 3.5 h after which no starting material was observed by HPLC. The mixture was cooled to 0° C. and methanol was added very slowly until no evolution of gas was observed. The mixture became homogeneous and then a precipitate began to form. The mixture was conc. In vacuo to a pale yellow solid which was triturated with water and collected by filtration to yield product 2.0 g (96% yield).

Preparation of Compound VIII:

To a suspension of Compound 29 (1.13 mmol, 1 eq.) in methylene chloride (30 mL) at 0° C. under nitrogen was added trifluoroacetic anhydride (3 eq.) followed by triethylamine (3 eq.). The reaction mixture gradually became homogeneous and stirred at 0° C. for 1 h then warmed to room temperature overnight. The mixture was diluted with methylene chloride and washed with water and brine. The organic phase was dried over magnesium sulfate, filtered and conc. In vacuo to a solid. This material was carried on without purification.

General Procedure for Ether Formation (General Structure IX):

VIII was dissolved in the appropriate alcohol (0.025 M) and heated to 80° C. in an oil bath. The reaction mixture was monitored for disappearance of starting material. The mixture was cooled to room temperature and the solvent removed in vacuo leaving a solid. The resulting solid was triturated with ether and collected by filtration. In some cases, the products were further purified using chromatographic techniques.

The following compounds were prepared according to the above general procedure:

Example 1

$R^5$=Oet, 18% purified yield; MS (m/z): 427 (M$^+$+1); $^1$H NMR (300 MHz, DMSO-d$_6$) δ (ppm): 1.148 (t, 3H), 1.94 (m, 2H), 3.46–3.52 (m, 4H), 4.53 (s, 2H), 4.60 (s, 2H), 4.73 (m, 2H), 4.91 (s, 2H), 7.36 (m, 3H), 7.48 (d, 1H), 7.64 (m, 2H), 7.90 (s, 1H), 8.55 (s, 1H), 9.47 (d, 1H).

Example 2

$R^5$=Ome, 95% yield; MS (m/z): 413 (M$^+$+1), 435 (M$^+$+Na); $^1$H NMR (300 MHz, DMSO-d$_6$) δ (ppm): 1.99 (m, 2H), 3.36 (s, 3H), 3.54 (m, 2H), 4.58 (s, 2H), 4.66 (s, 2H), 4.79 (m, 2H), 4.96 (s, 2H), 7.40–7.49 (m, 2H), 7.52 (d, 1H), 7.65–7.84 (m, 2H), 7.98 (s, 1H), 8.60 (s, 1H), 9.51 (d, 1H).

Example 3

$R^5$=OiPr, 31% yield; MS (m/z): 441 (M$^+$+1); $^1$H NMR (300 MHz DMSO-d$_6$) δ (ppm): 1.15 (d, 6H, 1.92 (m, 2H), 3.45 (m, 2H), 3.67 (m, 1H), 4.52 (s, 2H), 4.61 (s, 2H), 4.73 (m, 2H), 4.89 (s, 2H), 7.3–7.39 (m, 2H0, 7.47 (d, 1H), 7.62–7.69 (m, 2H), 7.89 (s, 1H), 8.54 (s, 1H), 9.47 (d, 1H).

Example 4

$R^5$=OCH(CH$_3$)CH$_2$CH$_3$, 25% yield; MS (m/z): 455 (M$^+$+1); $^1$H NMR (300 MHz, CDCl$_3$) δ (ppm): 0.98(t, 3H), 1.26 (d, 3H), 1.65 (m, 2H), 2.03 (m, 2H), 3.56 (m, 2H), 4.095 (m, 1H), 4.24 (s, 2H), 4.57 (m 2H), 4.70 (m, 2H), 4.71 (s, 2H), 6.12 (s, 1H), 7.33 (t, 1H), 7.42–7.58 (m, 4H), 7.75 (s, 1H), 9.48 (d, 1H).

Example 5

$R^5$=(R)—OCH(CH$_3$)CH$_2$CH$_3$, 61% yield; MS (m/z): 455 (M$^+$+1); $^1$H NMR (300 MHz, CDCl$_3$) δ (ppm): 0.98(t, 3H), 1.26 (d, 3H), 1.65 (m, 2H), 2.03 (m, 2H), 3.56 (m, 2H), 4.095 (m, 1H), 4.24 (s, 2H), 4.57 (m 2H), 4.70 (m, 2H), 4.71 (s, 2H), 6.12 (s, 1H), 7.33 (t, 1H), 7.42–7.58 (m, 4H), 7.75 (s, 11), 9.48 (d, 1H).

Example 6

$R^5$=(S)—OCH(CH$_3$)CH$_2$CH$_3$, 93% yield; MS (m/z): 455 (M$^+$+1); $^1$H NMR (300 MHz, CDCl$_3$) δ (ppm): 0.98(t, 3H), 1.26 (d, 3H), 1.65 (m, 2H), 2.03 (m, 2H), 3.56 (m, 2H), 4.095 (m, 1H), 4.24 (s, 2H), 4.57 (m 2H), 4.70 (m, 3H), 4.71 (s, 2H), 6.12 (s, 1H), 7.33 (t, 1H), 7.42–7.58 (m, 4H), 7.75 (s, 1H), 9.48 (d, 1H).

Example 8

$R^5$=O-nPr, 62% yield; MS (m/z): 441 (M$^+$+1), 462 (M$^+$+Na); $^1$H NMR (300 MHz, DMSO-d$_6$) δ (ppm): 0.88 (t, 3H), 1.55 (m, 2H), 1.933 (m, 2H), 3.36–3.58 (m, 4H), 4.53 (s, 2H), 4.61 (s, 2H), 4.73 (m, 3H), 4.90 (s, 2H), 7.33–7.39 (m 2H), 7.47 (d, 1H), 7.62–7.70 (m, 2H), 8.54 (s, 1H), 9.47 (d, 1H).

Example 9

$R^5$=O-nBu, 92% yield; MS (m/z): 455 (M$^+$+1); $^1$H NMR (300 MHz 30 DMSO-d$_6$) δ (ppm): 0.854 (t, 3H), 1.34 (m, 2H), 1.52 (m, 2H), 1.93 (m, 2H), 3.48 (m, 2H), 4.52 (s, 2H), 4.60 (s, 2H), 4.73 (m, 3H), 4.89 (s, 2H), 7.30–7.42 (m, 2H), 7.47 (d, 1H), 7.62–7.70 (m, 2H), 7.89 (s, 1H), 8.54 (s, 1H), 9.47 (d, 1H).

Example 17

$R^5$=O-tBu, 35% yield; MS (m/z): 455 (M$^+$+1), 477 (M$^+$+Na); $^1$H NMR (300 MHz, DMSO-d$_6$) δ (ppm): 1.28 (s, 9H), 1.97 (m, 2H), 3.62 (m, 2H), 4.56 (s, 2H), 4.52 (s, 2H), 4.77 (m, 3H), 4.94 (s, 2H), 7.35–7.72 (3m, 3H), 7.72 (m, 2H), 7.90 (s, 1H), 8.8.57 (s, 1H), 9.50 (d, 1H).

Example 25

$R^6$=Set, 96% yield; MS (m/z): 443 (M$^+$+1); $^1$H NMR (300 MHz DMSO-d$_6$) δ (ppm): 1.17 (t, 3H), 1.93 (m, 2H), 2.42 (q, 2H), 3.48 (m, 2H), 3.93 (s, 2H), 4.52 (s, 2H), 4.72 (m, 3H), 4.89 (s, 2H), 7.33–7.49 (m, 3H), 7.65 (m, 2H), 7.88 (s, 1H), 8.56 (s, 1H), 9.46 (d, 1H).

Example 26

$R^6$=SOCH(CH$_3$)$_2$, MS (m/z): 494 (M$^+$+Na); $^1$H NMR (300 MHz DMSO-d$_6$) δ (ppm): 1.21 (dd, 6H), 1.93 (m, 2H), 2.82 (m, 1H), 3.49 (m, 2H), 4.12 (d, 1H), 4.23 (d, 1H), 2.52 (s, 2H), 4.75 (m, 3H), 4.88 (s, 2H), 7.33–7.45 (m, 2H), 7.55 (d, 1H), 7.65 (d, 1H), 7.71 (d, 1H), 7.94 (s, 1H), 8.58 (s, 1H), 9.47 (d, 1H).

Example 27

$R^6$=SCH(CH$_3$)$_2$, MS (m/z): 457 (M$^+$+1), 479 (M$^+$+Na); $^1$H NMR (300 MHz, CDCl$_3$) δ (ppm): 1.31 (d, 6H), 2.34 (m, 2H), 2.86 (m, 1H), 3.98 (s, 2H), 4.29 (s, 2H), 4.45 (m, 1H), 4.74 (m, 2H), 4.92 (s, 2H), 6.07 (s, 1H), 7.39 (m, 2H), 7.51 (m, 2H), 7.57 (m, 1H), 7.80 (s, 1H), 9.53 (d, 1H).

Example 37

$R^6$=nPrS (Trifluoroacetate), 66% yield; $^1$H NMR (DMSO-d6, 300 MHz): δ 0.92 (t, 3H), 1.58 (q, 2H), 2.29 (m, 2H), 2.44 (t, 2H), 3.95 (s, 2H), 4.53 (m, 4H), 4.82 (m, 2H), 4.93 (s, 2H), 7.41 (m, 2H), 7.52 (d, 1H), 7.60 (d, 1H), 7.72 (d, 1H), 7.93 (s, 1H), 8.62 (s, 1H), 9.51 (d, 1H).

Example 38

$R^6$=S(C$_5$H$_4$N), 51% yield; MS (ESI): m/e 514 (M+Na)$^+$, $^1$H NMR (DMSO-d6, 300 MHz): δ 1.014 (m, 2H), 3.45 (m, 2H), 4.51 (s, 2H), 4.60 (s, 2H), 4.72 (m, 3H), 4.85 (s, 2H), 7.11 (m, 1H), 7.30–7.41 (m, 3H), 7.54–7.67 (m, 4H), 8.02 (s, 1H), 8.48 (d, 1H, J=3.97), 8.55 (s, 1H), 9.46 (d, 1H, J=7.36).

Example 39

$R^6$=S(C4H3N2), 52% yield; MS (m/z): 493 (M$^+$+H); $^1$H NMR (300 MHz, DMSO-d$_6$) δ (ppm): 1.93 (m, 2H), 3.45 (m, 2H), 4.51 (s, 3H), 4.60 (s, 2H), 4.72 (m, 2H), 4.88 (s, 2H), 7.22 (t, 1H), 7.32–7.68 (m, 6H), 8.05 (s, 1H), 8.55 s, 1H), 8.66 (d, 1H), 9.46 (d, 1H).

Example 30

$R^5$=H, 44% yield; $^1$H NMR (300 MHz, DMSO-d$_6$) δ (ppm): 4.13 (s, 2H), 4.64 (s, 2H), 4.89 (s, 2H), 7.28–7.42 (m, 3H), 7.53 (d, 1H), 7.64 (d, 1H), 7.89 (s, 1H), 8.49 (s, 1H), 9.34 (d, 1H), 11.83 (s, 1H).

Example 31

$R^5$=Oet, 83% yield; $^1$H NMR (300 MHz, DMSO-d$_6$) δ (ppm): 1.18 (t, 3H), 3.55 (q, 2H), 4.62 (s, 2), 4.93 (s, 2H), 7.34–7.46 (m, 3H), 7.58 (d, 1H), 7.68 (d, 1H), 7.92 (s, 1H), 8.54 (s, 1H), 9.39 (d, 1H), 11.91 (s, 1H).

Example 32

$R^5$=OiPr, 41% purified yield; $^1$H NMR (300 MHz, DMSO-d$_6$) δ (ppm) 1.15 (d, 6H), 3.68 (m, 1H), 4.13 (s, 2H), 4.59 (s, 2H), 4.89 (s, 2H), 7.28–7.42 (m, 3H), 7.54 (d, 1H), 7.64 (d, 1H), 7.88 (d, 1H), 8.49 (s, 1H), 9.35 (d, 1H), 11.87 (s, 1H).

Preparation of Compound XI:

To a suspension of aluminum chloride (3 eq.) in 1,2-dichloroethane/methylene chloride (1:1, 8 mL) was added acetyl chloride (3 eq.) under nitrogen. The reaction mixture became homogeneous and was cooled to 0° C. in an ice bath. A suspension of B (0.84 mmol, 1 eq.) in methylene chloride (3 mL) was added drop wise and the mixture turned brown in color. The ice bath was removed and the reaction mixture was warmed to room temperature. The mixture was heated to reflux for 2 h then cooled to room temperature. HPLC showed no starting material present. The mixture was poured over ice water and conc. HCl (5 mL) was added. A precipitate formed and was collected by filtration and dried. 340 mg (89% yield), MS (m/z): 453 (M$^+$+1); $^1$H NMR (300 MHz, DMSO-d$_6$) δ (ppm): 2.02 (s, 3H), 2.18 (m, 2H), 2.74 (s, 3H), 4.12 (m, 2H), 4.56 (s, 2H), 4.83 (m, 2H), 5.05 (s, 2H), 7.43 (m, 2H), 7.68 (d, 1H), 7.86 (d, 1H), 8.17 (d, 1H), 8.56 (s, 1H), 8.72 (1H), 9.53 (d, 1H).

Example 33

To a suspension of XI (0.18 mmol, 1 eq.) in THF (6 mL) under nitrogen was added lithium borohydride (10 eq.) at 0° C. The reaction mixture was stirred at 0° C. for 1 h then warmed to room temperature for 4 h. The mixture was cooled to 0° C. and methanol was added slowly drop wise. Vigorous evolution of gas was observed during the quenching of excess borohydride. The mixture was stirred at room temperature overnight. The reaction mixture was diluted with ethyl acetate and washed with water and brine. The organic layer was dried over magnesium sulfate, filtered and concentrated in vacuo to a white solid, 69 mg (90% yield). MS (m/z): 413 (M$^+$+1), 435 (M$^+$+Na); $^1$H NMR (300 MHz, DMSO-d$_6$) δ (ppm): 1.41 (d, 3H), 1.92 (m, 2H), 3.46 (m, 2H), 4.52 (s, 2H), 4.71 (m, 3H), 4.89 (s, 3H), 5.18 (s, 1H), 7.32–7.39 (m, 2H), 7.50 (d, 1H), 7.64 (m, 2H), 7.89 (s, 1H), 8.55 (s, 1H), 9.46 (d, 1H).

The following compounds were prepared according to the general procedure for ether formation using the tri-trifluoroacetate intermediates:

Example 10

$R^5$=Oet, 68% yield; MS (m/z): 441 (M$^+$+1), 395 (M+—OCH$_2$CH$_3$); $^1$H NMR (300 MHz, DMSO-d$_6$) δ (ppm): 1.08 (t, 3H), 1.41 (d, 3H), 1.93 (m, 2H), 3.47 (m, 2H), 4.52 (s, 2H), 4.60 (m, 1H), 4.73 (m, 2H), 4.90 (m, 2H), 7.33–7.39 (m, 2H), 7.47 (d, 1H), 7.63 (d, 1H), 7.69 (d, 1H), 7.86 (s, 1H), 8.55 (s, 1H), 9.47 (d, 1H).

Reverse phase HPLC separation of 10 yielded isomers 11 and 12.

Example 11 (Chiral)

$R^5$=Oet, MS (m/z): 441 (M$^+$+1), 395 (M+—OCH$_2$CH$_3$).

Example 12 (Chiral):

$R^5$=Oet, MS (m/z) 441 (M$^+$+1), 395 (M+—OCH$_2$CH$_3$).

Example 13

$R^5$=Ome, 76% yield; MS (m/z): 427 (M$^+$+1); $^1$H NMR (300 MHz DMSO-d$_6$) δ (ppm): 1.45 (d, 3H), 1.98 (m, 2H), 3.14 (s, 3H), 3.50 (m, 2H), 4.58 (m, 3H), 7.75 (m, 2H), 4.93

(s, 2H), 7.33 (m, 2H), 7.48 (d, 1H), 7.67 (d, 1H), 7.72 (d, 1H), 7.88 (s, 1H), 8.58 (s, 1H), 9.49 (d, 1H).

Example 15

$R^5$=Obu, 73% yield; $^1$H NMR (300 MHz, DMSO-$d_6$) δ (ppm): 0.81 (t, 3H), 1.27–1.43 (m, 7H), 1.93 (m, 2H), 3.48 (m, 2H), 4.53 (s, 2H), 4.58 (m, 1H), 4.73 (m, 4H), 4.92 (m, 2H), 7.33–7.39 (m, 2H), 7.46 (d, 1H), 7.63 (d, 1H), 7.69 (d, 1H), 7.86 (s, 1H), 8.55 (s, 1H), 9.47 (d, 1H).

Example 16

$R^5$=OiPr, 63% yield; $^1$H NMR (300 MHz, DMSO-$d_6$) δ (ppm): 1.01 (d, 3H), 1.10 (d, 3H), 1.38 (d, 3H), 1.95 (m, 2H), 3.47 (m, 2H), 3.98 (q, 1H), 4.26 (m, 1H), 4.52 (s, 2H), 4.74 (m, 3H), 4.90 (m, 2H), 7.33–7.39 (m, 2H), 7.48 (d, 1H), 7.62–7.69 (m, 2H), 7.87 (s, 1H), 8.54 (s, 1H), 9.47 (d, 1H).

Example 35

$R^5$=H, 98% yield; MS (m/z): 455 ($M^+$+1), 337 ($M^+$–$H_2O$); $^1$H NMR (300 MHz, DMSO-$d_6$) δ (ppm): 1.45 (d, 3H), 4.25 (m, 3H), 4.86 (s, 2H), 5.16 (d, 1H), 7.28–7.39 (m, 2H), 7.43 (d, 1H), 7.56 (d, 1H), 7.66 (d, 1H), 7.92 (s, 1H), 8.49 (s, 1H), 9.35 (d, 1H), 11.78 (s, 1H).

Example 36

$R^5$=Ome, 50% yield; MS (m/z): 369 ($M^+$+1); $^1$H NMR (300 MHz, DMSO-$d_6$) δ (ppm): 1.43 (d, 3H), 3.16 (s, 3H), 4.15 (m, 2H), 4.49 (m, 1H), 4.93 (s, 2H), 7.32–7.40 (m, 3H), 7.58 (d, 1H), 7.67 (d, 1H), 7.84 (s, 1H), 8.50 (s, 1H), 9.44 (d, 1H), 11.87 (s, 1H).

Example 34

$R^5$=H, (77% yield over 2 steps); MS (m/z): 427 ($M^+$+1), 409 ($M^+$–$H_2O$); $^1$H NMR (300 MHz, DMSO-$d_6$) δ (ppm): 0.848 (t, 3H), 1.70 (m, 2H), 1.93 (m, 2H), 3.47 (m, 2H), 4.52 (s, 2H), 4.61 (m, 1H), 4.72 (m, 3H), 4.89 (s, 2H), 5.14 (s, 1H), 7.29–7.39 (m, 2H), 7.44 (d, 1H), 7.64 (m, 2H), 7.87 (s, 1H), 8.54 (s, 1H), 9.46 (d, 1H).

General Procedure for Ester formation of Example 3: An oven dried, 3-L, 3-necked, round-bottomed flask equipped with a mechanical stirrer, a three-way stopcock connected to an argon balloon and an immersion thermometer was charged with compound 3 (148.6 mmol) followed by anhydrous N,N-dimethylacetamide (654 mL). 4-(Dimethylamino)pyridine (DMAP) (0.5 eq.), Amino acid (2.5 eq.) and 1-[3-(dimethylamino)propyl]-3-ethylcarbodiimide hydrochloride (2.5 eq) were added sequentially at 35° C. to the clear red colored solution. The reaction suspension heated to 42–45° C. for 2 h and additional quantities of DMAP (0.08 eq.), Amino Acid (0.5 eq.) and 1-[3-(dimethylamino)propyl]-3-ethylcarbodiimide hydrochloride (0.5 eq.) were added sequentially. After 1.5 h, the reaction mixture was cooled to 0–5° C. and quenched with water. The cooling bath was removed and the resulting pale yellow suspension was stirred at room temperature for 1 h. The suspension was filtered, washed with water to pH=8 and dried overnight using house vacuum. The pale yellow solid was not dried completely and dissolved in methylene chloride and the water layer was separated. The organic phase was washed with brine, dried over MgSO4, filtered over celite and concentrated using a rotary evaporator to afford the crude solid. The crude material was again dissolved in methylene chloride and transferred into a 3-L, 3-necked round-bottomed flask, which was equipped with a mechanical stirrer. Ethyl acetate (IL) was added drop wise at room temperature to the clear red colored solution for 70 min. with continuous stirring. After the addition of ethyl acetate (15 mL), a precipitate formed. The slurry was stirred for 2.5 h followed by collection of the solid by filtration. The precipitate was washed sequentially with ethyl acetate, a mixture of ethyl acetate/methyl-tert butyl ether (3:2) and methyl t-butyl ether and dried to an off-white solid. 78% yield.

Example 18

MS (m/z): 498 ($M^+$+1)

Example 19

MS (m/z): 566 ($M^+$+1)

Example 20

MS (m/z): 569 ($M^+$+1)

Example 21

MS (m/z): 512 ($M^+$+1)

Example 22

MS (m/z): 554 ($M^+$+1)

Example 23

MS (m/z): 526 ($M^+$+1)

Example 24

MS (m/z): 554 ($M^+$+1)

Preparation of XIII:

Example 31 (0.33 mmol) was dissolved in DMF (10 mL) and half the volume was removed by distillation. The flask was cooled to room temperature and sodium hydride (1 eq.) was added and the mixture was stirred for 1 h. Mesylglycidol (1.5 eq.) was added and the mixture warmed to 50° C. for 24 h then cooled to room temperature. The mixture was filtered and the solvent removed in vacuo. The reaction mixture was purified by column chromatography on silica gel to yield XIII in 73% yield. 1.19 (t, 3H), 2.78 (t, 1H), 3.53 (m, 4H), 4.53 (s, 2H), 4.65 (s, 2H), 4.78 (dd, 1H), 4.96 (s, 2H), 5.20 (d, 1H), 7.35–7.47 (m, 2H), 7.51 (d, 1H), 7.68 (d, 1H), 7.75 (d, 1H), 7.95 (s, 1H), 8.62 (s, 1H), 9.55 (d, 1H).

Example 7

Compound XIII (100 mg) was dissolved in THF (10 mL) and triethyl borohydride (2 mL) was added drop wise. The reaction mixture was heated to 70° C. for 4 h. The mixture was cooled to room temperature and 1N HCl was added. The solvent was removed in vacuo and the material was taken up in a mixture of methanol/water. The resulting precipitate was collected by filtration and dried. 1.19 (t, 3H), 1.25 (d, 3H), 3.55 (q, 2H), 4.13 (m, 2H), 4.58 (s, 2H), 4.61 (s, 2H), 4.64 (s, 2H), 4.93 (s, 2H), 4.97 (t, 1H), 7.34–7.45 (m, 2H), 7.49 (d, 1H), 7.69 (t, 2H), 7.92 (s, 1H), 8.57 (s, 1H), 9.50 (d, 1H).

Example 14

To a suspension of XIV (0.75 mmol) in methylene chloride/methanol/HMPA (4:2:1 mL), was added cesium carbonate (4.0 eq.). The reaction mixture was stirred for 30 min. followed by addition of acetaldehyde. Additional acetaldehyde was added with little change observed by TLC. The mixture was diluted with methylene chloride and washed with water and brine. The organic phase was dried over magnesium sulfate, filtered, and concentrated in vacuo. The crude product XV was isolated by column chromatography (33% yield). XV (0.3 mmol) was dissolved in methylene chloride and cooled to 0° C. Ethanethiol (2 drops) and trifluoroacetic acid (TFA)(1 drop) were added to the solution and the mixture stirred at 0° C. for 1 h. The mixture was warmed to room temperature and stirred for 1 h. Additional TFA (2 drops) was added and the reaction mixture and after 30 minutes the reaction was complete. The product was purified by column chromatography on silica gel using methylene chloride/ethyl acetate. A single diastereomer was isolated 65 mg (53%). 0.52 (d, 3H), 1.21 (t, 3H), 2.47 (q, 2H), 3.96 (s, 2H), 4.49 (s, 1H), 4.86 (m, 1H), 4.94 (s, 2H), 6.18 (s, 1H), 7.35–7.45 (m, 3H), 7.64 (d, 1H), 7.72 (d, 1H), 7.92 (s, 1H), 8.57 (s, 1H), 9.41 (d, 1H), 10.99 (s, 1H).

Preparation of XVII:

To a solution of hexamethylenetetraamine (1.6 g, 11.4 mmol) in TFA was added XVI (2.0 g, 4.6 mmol) at 60–65° C. After stirring 2 hours the reaction was cooled to room temperature, followed by the drop wise addition into 2N $H_2SO_4$-acetone (150 mL) (2:1). The solid was collected, suspended in dioxolane (150 mL) and heated to reflux for 30 minutes. The undissolved material was removed by filtration and the solvent was concentrated to approximately 25 mL. MeOH (50 mL) was added to precipitate the product, which was collected and dried to give 700 mg of an off yellow solid. MS $ES^+$ 467 (M+1).

Example 28

A suspension of the XVII (500 mg, 1.1 mmol) in $CHCl_3$/methanol (60 mL, 5/1) was added solid $NaBH_4$ (200 mg). The solution was stirred at room temperature for 4 h. The $CHCl_3$ was removed at reduced pressure followed by the addition of 2 N HCl. The solution was stirred for 2 h then collected and dried to give 420 mg of an off white solid. MS ($ES^+$) 469 (M+1). The crude alcohol was suspended in $CHCl_3$-MeOH (25 mL+10 mL) then added 0.7 mL of 1 M NaOMe followed by stirring 12 hour at room temperature. The solvent was concentrated, the solid triturated with MeOH and the product collected to give the diol 420 mg (84%). $^1H$ NMR (DMSO-d6, 300 MHz): δ 3.8 (m, 2H), 4.55 (s, 2H), 4.63 (d, 2H), 4.75 (m, 2H), 4.97 (s, 2H), 5.0, (m, 1H), 5.23 (m, 1H), 7.34–7.51 (m, 4H), 7.68 (m, 2H), 7.94 (s, 1H), 8.57 (s, 1H), 9.51 (d, 1H). MS ($ES^+$) 385 (M+1).

Example 24

A suspension of Example 28 (50 mg, 0.13 mmol) in $CHCl_3$ was added camphorsulfonic acid (30 mg, 0.26 mmol) and ethane thiol (0.39 mmol), followed by stirring 12 under nitrogen. Excess $CHCl_3$ was added and then the solution was washed with 2 M $Na_2CO_3$ solution, water, brine and dried ($MgSO_4$). The solvent was concentrated, and the product collected after triturating with MeOH. $^1H$ NMR (DMSO-d6, 300 MHz): δ 1.1, 2.3, (m, 2H), 3.85 (m, 2H), 4.0 (s, 2H), 5.5 (s, 2H), 4.8 (m, 2H), 4.9 (s, 2H), 5.0 (t, 1H), 7.35–7.5 (m, 4H), 7.7 (m, 2H), 8.6 (s, 1H), 9.5 (d, 1H). (m, 3H), MS (ES+) 429,451 (M+1, +23).

Example 40

To a solution of Example 3 (210 mg, 0.48 mmol) in DMF (10 mL) was added DMAP (1 mg), $Et_3N$ (267 uL, 1.92 mmol) and tBDMSCl (220 mg, 1.47 mmol). After stirring 20 h, the mixture was taken up in EtOAc and successively washed with aqueous $NaHCO_3$, water and brine. The organic layer was dried over $MgSO_4$, filtered and evaporated to afford a residue that was purified by column chromatography (silica gel, 10% EtOAc/hexane) to give 225.1 mg of intermediate XVIII (70%).

A mixture of XVIII (68.1 mg, 0.10 mmol) and paraformaldehyde (63.1 mg, 2.1 mmol) in pyridine (4 mL) was treated with a 0.25M solution of Triton B in pyridine (100 uL, 0.025 mmol). After stirring for 2 h, additional Triton B in pyridine (150 uL, 0.038 mmol) was added. After 1 h, the mixture was taken up in EtOAc and exhaustively washed with aqueous CuSO4. After washing with water, aqueous $NaHCO_3$, and brine, the organic layer was dried over $MgSO_4$, filtered and evaporated to afford a residue that was purified by column chromatography (silica gel, 22% EtOAc/hexane) to give 45.2 mg of IXX (64%) which had the following spectral properties: $^1H$ NMR (DMSO-$d_6$) δ 9.42 (d, 1H, J=7.7), 7.97 (s, 1H), 7.75–7.72 (m, 2H), 7.52 (d, 1H, J=8.5), 7.44 (dd, 1H, J=7.7,7.5), 7.36 (dd, 1H, J=7.7, 7.5), 5.13 (m, 1H), 5.04 (s, 2H), 4.77 (m, 1H), 4.70 (s, 2H), 4.10 (m, 1H), 3.76 (sep, 1H, J=6.1), 3.54 (m, 1H), 3.44 (m, 1H), 3.31 (m, 3H), 1.79 (m, 2H), 1.22 (m, 6H), 1.07 (s, 9H), 0.85 (s, 9H), 0.52 (s, 6H), 0.00 (s, 3H), −0.03 (s, 3H); MS n/z 699 (M+H).

To a solution of XXI (22.5 mg, 0.032 mmol) in iPrOH (10 mL) was added TMSCl (100 uL), and the mixture was stirred for 2.5 h. After evaporation of solvent, the residue was triturated with ether (3×1 mL) and dried to afford 10.8 mg of Example 40 (72%) which had the following spectral properties: $^1H$ NMR (DMSO-$d_6$) 9.49 (d, 1H, J=7.7), 8.59 (s, 1H), 7.96 (s, 1H), 7.80 (d, 1H, J=7.3), 7.77 (d, 1H, J=8.5) 7.55 (d, 1H, J=7.3),7.45 (m, 1H), 7.37 (m, 1H), 4.98 (m, 3H), 4.78 (m, 2H), 4.70 (s, 2H), 4.20–4.16 (m, 2H), 3.76 (sep, 1H, J=6.1), 3.38 (m, 11H), 3.36–3.25 (m, 2H), 1.80 (m, 2H), 1.23 (d, 6H, J=6.1); MS m/z 471 (M+H).

Inhibition of Vascular Endothelial Growth Factor Receptor Kinase Activity

Fused pyrrolocarbazole compounds were examined for their inhibitory effects on the kinase activity of baculovirus-expressed VEGF receptor (human flk-1, KDR, VEGFR2) kinase domain using the procedure described for the trkA kinase ELISA assay described below. The kinase reaction mixture, consisting of 50 mM Hepes, pH 7.4, 40 μM ATP, 10 mM $MnCl_2$, 0.1% BSA, 2% DMSO, and various concentrations of inhibitor, was transferred to PLC-γ/GST-coated plates. VEGFR kinase was added and the reaction was allowed to proceed for 15 min. at 37° C. Detection of phosphorylated product was accomplished by addition of anti-phosphotyrosine antibody (UBI). A secondary enzyme-conjugated antibody was delivered to capture the antibody-phosphorylated PLC-γ/GST complex. The activity of the bound enzyme was measured via an amplified detection system (Gibco-BRL). Inhibition data were analyzed using the sigmoidal dose-response (variable slope) equation in GraphPad Prism. Results are summarized in Table III.

TABLE III

VEGFR Inhibition

| Compound | VEGFR2 (IC$_{50}$ or % inh. @ 300 nM) |
|---|---|
| A | 107 |
| B | 48 |
| C | 17% |
| D | 200 |
| 1 | 4 |
| 2 | 17 |
| 3 | 7 |
| 4 | 12 |
| 5 | 12 |
| 6 | 19 |
| 7 | 25 |
| 8 | 13 |
| 9 | 18 |
| 10 | 83 |
| 11 | 65 |
| 12 | 240 |
| 13 | 73 |
| 14 | 72 |
| 15 | 130 |
| 16 | 411 |
| 17 | 11 |
| 18 | 23 |
| 19 | 60% |
| 20 | 31 |
| 21 | 48% |
| 22 | 18 |
| 23 | 57% |
| 24 | 31% |
| 25 | 21 |
| 26 | 31% |
| 27 | 57 |
| 28 | 34% |
| 29 | 208 |
| 30 | 302 |
| 31 | 77 |
| 32 | 33% |
| 33 | 111 |
| 34 | 7 |
| 35 | 37% |
| 36 | 12% |
| 37 | 37% |
| 38 | 45% |
| 39 | 13% |
| 40 | 16 |

Inhibition of Mixed Lineage Kinase-1 (MLK1) Activity

The kinase activity of MLK1 was assessed using the Millipore Multiscreen TCA "in-plate" format as described for protein kinase C (Pitt & Lee, *J. Biomol. Screening*, 1: 47–51, 1996). Briefly, each 50-μl assay mixture contained 20 mM Hepes, pH 7.2, 5 mM EGTA, 15 mM MgCl$_2$, 25 mM β-glycerophosphate, 60 μM ATP, 0.25 μCi [γ-$^{32}$P]ATP, 0.1% BSA, 500 μg/ml myelin basic protein (UBI #13–104), 2% DMSO, 1 μM of test compound, and 1 μg/ml of baculoviral GST-MLK1$_{KD}$. Samples were incubated for 15 min at 37° C. The reaction was stopped by adding ice cold 50% TCA and the proteins were allowed to precipitate for 30 min at 4° C. The plates were then washed with ice cold 25% TCA. Supermix scintillation cocktail was added, and the plates were allowed to equilibrate for 1–2 hours prior to counting using the Wallac MicroBeta 1450 PLUS scintillation counter.

Inhibition of Mixed Lineage Kinase-2 (MLK2) Activity

Assays were performed using the Millipore Multiscreen plate format as described for MLK1. Each 50-μl assay mixture contained 20 mM Hepes, pH 7.2, 5 mM EGTA, 15 mM MgCl$_2$, 25 mM β-glycerophosphate, 100 μM ATP, 0.25 μCi [γ-$^{32}$P]ATP, 0.1% BSA, 500 μg/ml myelin basic protein (UBI #13–104), 2% DMSO, various concentrations of test compound, and 3 μg/ml of baculoviral GST-MLK2$_{KDLZ}$. Samples were incubated for 15 min. at 37° C. The reaction was stopped by adding ice cold 50% TCA and the proteins were allowed to precipitate for 30 min at 4° C. The plates were then washed with ice cold 25% TCA. Supermix scintillation cocktail was added, and the plates were allowed to equilibrate for 1–2 hours prior to counting.

Inhibition of Mixed Lineage Kinase-3 (MLK3) Activity

Assays were performed using the Millipore Multiscreen plate format as described for MLK1. Briefly, each 50-μl assay mixture contained 20 mM Hepes, pH 7.2, 5 mM EGTA, 15 mM MgCl$_2$, 25 mM β-glycerophosphate, 100 μM ATP, 0.25 μCi [γ-$^{32}$P]ATP, 0.1% BSA, 500 μg/ml myelin basic protein (UBI #13–104), 2% DMSO, various concentrations of test compound, and 2 μg/ml of baculoviral GST-MLK3$_{KD}$. Samples were incubated for 15 min at 37° C. The reaction was stopped by adding ice cold 50% TCA and the proteins were allowed to precipitate for 30 min at 4° C. The plates were then washed with ice cold 25% TCA. Supermix scintillation cocktail was added, and the plates were allowed to equilibrate for 1–2 hours prior to counting.

TABLE IV

MLK Inhibition

IC50 (nM) or % Inhibition @ 100 nM

| Compound | MLK1 | MLK2 | MLK3 |
|---|---|---|---|
| A | 22 | 39% | 8 |
| B | 31 | 46% | 17 |
| C | 8% | 0% | 30% |
| D | 45 | | 43% |
| 1 | 21 | | 4 |
| 2 | 15 | | 8 |
| 3 | 17 | | 9 |
| 4 | 15 | | 4 |
| 5 | 27 | 45% | 16 |
| 6 | 38 | 51% | 19 |
| 7 | 85% | | 30 |
| 8 | 19 | 76% | 13 |
| 9 | 26 | | 15 |
| 10 | 37 | | 15 |
| 11 | 78 | | 20 |
| 12 | 28 | 131 | 16 |
| 13 | 20 | 62% | 26 |
| 14 | 93% | | 9 |
| 15 | 41 | | 27 |
| 16 | 66% | | 49% |
| 17 | 35 | 50% | |
| 18 | 47 | | 23 |
| 19 | 44% | 28% | |
| 20 | 42 | 229 | 32 |
| 21 | 40% | | |
| 22 | 74 | 170 | 28 |
| 23 | 31% | | |
| 24 | 62% | | 55% |
| 25 | 22 | | 12 |
| 26 | 59 | | |
| 27 | 22 | | |
| 28 | 76 | | 74 |
| 29 | 9 | 64% | 5 |
| 30 | 30 | | |
| 31 | 46 | | 29 |
| 32 | 24 | | 19 |
| 33 | 50 | | 16 |
| 34 | 45% | | 32% |
| 35 | 60% | | 62% |
| 36 | 26 | | 41% |
| 37 | 17 | | |

TABLE IV-continued

| | MLK Inhibition | | |
| | IC50 (nM) or % Inhibition @ 100 nM | | |
| Compound | MLK1 | MLK2 | MLK3 |
| --- | --- | --- | --- |
| 38 | 58% | | 30 |
| 39 | 55% | | 56% |
| 40 | 21 | 86 | |

Inhibition of trkA Tyrosine Kinase Activity

Selected isomeric fused pyrrolocarbazole and isoindolone compounds can be tested for their ability to inhibit the kinase activity of baculovirus-expressed human trkA cytoplasmic domain using an ELISA-based assay as previously described (Angeles et al., Anal. Biochem. 236: 49–55, 1996). Briefly, the 96-well microtiter plate is coated with substrate solution (recombinant human phospholipase C-γ1/glutathione S-transferase fusion protein (Rotin et al., EMBO J., 11: 559–567, 1992). Inhibition studies are performed in 100 μl assay mixtures containing 50 mM Hepes, pH 7.4, 40 μM ATP, 10 mM MnCl$_2$, 0.1% BSA, 2% DMSO, and various concentrations of inhibitor. The reaction is initiated by addition of trkA kinase and allowed to proceed for 15 minutes at 37° C. An antibody to phosphotyrosine (UBI) is then added, followed by a secondary enzyme-conjugated antibody, alkaline phosphatase-labelled goat anti-mouse IgG (Bio-Rad). The activity of the bound enzyme is measured via an amplified detection system (Gibco-BRL). Inhibition data are analyzed using the sigmoidal dose-response (variable slope) equation in GraphPad Prism. The concentration that resulted in 50% inhibition of kinase activity is referred to as "IC$_{50}$".

Inhibition of NGF-Stimulated trk Phosphorylation in a Whole Cell Preparation

The inhibition of NGF-stimulated phosphorylation of trk by the compounds of the present invention can be performed using a modified procedure, as described below, from that previously described (see U.S. Pat. No. 5,516,771). NIH3T3 cells transfected with trkA are grown in 100 mm dishes. Subconfluent cells are serum-starved by replacing media with serum-free 0.05% BSA-DMEM containing compound (100 nM and 1 μM) or DMSO (added to controls) for one hour at 37° C. NGF (Harlan/Bioproducts for Science) is then added to the cells at a concentration of 10 ng/ml for 5 minutes. Cells are lysed in buffer containing detergent and protease inhibitors. Clarified cell lysates are normalized to protein using BCA method and immunoprecipitated with anti-trk antibody. Polyclonal anti-trk antibody is prepared against a peptide corresponding to the 14 amino acids at the carboxy terminus of trk (Martin-Zanca et al., Mol. Cell. Biol. 9: 24–33, 1989).

The immune complexes are collected on Protein A Sepharose beads (Sigma Chem. Co., St. Lois, Mo.), separated by SDS polyacrylamide gel electrophoresis (SDS-PAGE), and transferred to a polyvinylidene difluoride (PVDF) membrane. The membrane is immunoblotted with anti-phosphotyrosine antibody (UBI), followed by incubation with horseradish peroxidase coupled goat anti-mouse IgG (Bio-Rad Laboratories, Hercules, Calif.). Phosphorylated proteins were visualized using ECL (Amersham Life Science, Inc., Arlington Heights, Ill.). The area of the trk protein band is measured and compared to NGF-stimulated control. The inhibition scoring system used, based on percent decrease in trk protein band, can be as follows: 0=no decrease; 1=1–25%; 2=26–49%; 3=50–75%; 4=76–100%.

Inhibition of Platelet Derived Growth Factor Receptor Kinase Activity

Isomeric fused pyrrolocarbazole and isoindolone compounds can examined for their inhibitory effects on the kinase activity of baculovirus-expressed PDGFβ receptor kinase domain using the trkA kinase ELISA described above. Assays are performed in substrate (PLC-γ/GST)-coated 96-well microtiter plates. Each 100-μl reaction mixture contains 50 mM HEPES, pH 7.4, 20 μM ATP, 10 mM MnCl$_2$, 0.1% BSA, 2% DMSO, and various concentrations of inhibitor. The reaction is initiated by addition of prephosphorylated recombinant human enzyme (10 ng/ml PDGFRβ) and allowed to proceed for 15 minutes at 37° C. The prephosphorylated enzyme is prepared prior to use by incubation of the kinase in buffer containing 20 μM ATP and 10 mM MnCl$_2$ for 1 hour at 4 C. Detection of phosphorylated product is done by adding horseradish peroxidase (HRP)-conjugated anti-phosphotyrosine antibody (UBI). The HRP substrate solution containing 3,3'-5,5'-tetramethylbenzidine and hydrogen peroxide is later added and the plates incubated for 10 minutes at room temperature. The reaction is quenched with acid and the resulting absorbance is read at 450 nm using a Microplate Bio-kinetics Reader (Bio-Tek Instrument EL 312e). Inhibition data are analyzed using the sigmoidal dose-response (variable slope) equation in GraphPad Prism.

Although the present invention has been described in considerable detail, those skilled in the art will appreciate that numerous changes and modifications may be made to the embodiments and preferred embodiments of the invention and that such changes and modifications may be made without departing from the spirit of the invention. It is therefore intended that the appended claims cover all equivalent variations as fall within the scope of the invention.

What is claimed is:

1. Compounds of Formula I:

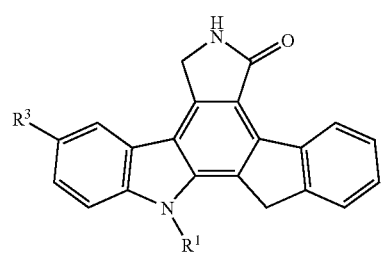

Formula I wherein $R^1$ and $R^3$ are in accordance with the following table:

| Cmpd | $R^1$ | $R^3$ |
| --- | --- | --- |
| 27 | CH$_2$CH$_2$CH$_2$OH | CH$_2$SCH(CH$_3$)$_2$ |
| 37 | CH$_2$CH$_2$CH$_2$OCOCF$_3$ | CH$_2$SCH$_2$CH$_2$CH$_3$ |
| 39 | CH$_2$CH$_2$CH$_2$OH | CH$_2$S(2-pyrimidyl). |

2. The compound of claim 1 wherein $R^1$ and $R^3$ are selected in accordance with the following table:

| Cmpd | R¹ | R³ |
|------|-----|-----|
| 37 | $CH_2CH_2CH_2OCOCF_3$ | $CH_2SCH_2CH_2CH_3$ |
| 39 | $CH_2CH_2CH_2OH$ | $CH_2S(2\text{-pyrimidyl})$. |

3. The compound of claim 1 wherein $R^1$ is $CH_2CH_2CH_2OH$ and $R^3$ is $CH_2SCH(CH_3)_2$.

4. The compound of claim 1 wherein $R^1$ is $CH_2CH_2CH_2OCOCF_3$ and $R^3$ is $CH_2SCH_2CH_2CH_3$.

5. The compound of claim 1 wherein $R^1$ is $CH_2CH_2CH_2OH$ and $R^3$ is $CH_2S(2\text{-pyrimidyl})$.

6. A pharmaceutical composition comprising a compound of claim 2 and a pharmaceutically acceptable excipient or carrier.

7. A method for treating prostate disorders which comprises administering to a host in need of such treatment a therapeutically effective amount of a compound of claim 2.

8. The method of claim 7 wherein the prostate disorder is prostate cancer or benign prostate hyperplasia.

* * * * *